US007818993B2

(12) United States Patent
Sun et al.

(10) Patent No.: US 7,818,993 B2
(45) Date of Patent: Oct. 26, 2010

(54) HIGH-PERFORMANCE FLEXIBLE HYDROGEN SENSORS

(75) Inventors: Yugang Sun, Naperville, IL (US); Hsien-Hau Wang, Downers Grove, IL (US)

(73) Assignee: UChicago Argonne, LLC, Argonne, IL (US)

(*) Notice: Subject to any disclaimer, the term of this patent is extended or adjusted under 35 U.S.C. 154(b) by 290 days.

(21) Appl. No.: 11/862,341

(22) Filed: Sep. 27, 2007

(65) Prior Publication Data

US 2009/0084159 A1 Apr. 2, 2009

(51) Int. Cl.
*G01N 7/00* (2006.01)
(52) U.S. Cl. .......................... 73/23.2; 977/748; 977/957
(58) Field of Classification Search ............. 977/748, 977/957; 73/23.2; 257/414
See application file for complete search history.

(56) References Cited

U.S. PATENT DOCUMENTS

| 7,237,429 | B2 * | 7/2007 | Monty et al. ............... 73/23.2 |
| 7,449,757 | B2 * | 11/2008 | Bradley et al. .............. 257/414 |
| 2004/0169243 | A1 * | 9/2004 | Tao et al. .................. 257/414 |
| 2005/0157445 | A1 * | 7/2005 | Bradley et al. .............. 361/226 |
| 2005/0184641 | A1 * | 8/2005 | Armitage et al. ............ 313/495 |
| 2006/0213251 | A1 | 9/2006 | Rinzler et al. |
| 2006/0263255 | A1 * | 11/2006 | Han et al. ................... 422/83 |
| 2007/0240491 | A1 * | 10/2007 | Pavlovsky et al. .......... 73/31.05 |
| 2009/0101996 | A1 * | 4/2009 | Bradley et al. .............. 257/414 |

OTHER PUBLICATIONS

Cao et al., "Highly bendable, transparent thin-film transistors that use carbon-nanotube-based conductors and semiconductors with elastomeric dielectrics", Adv. Mater. 2006, 18, pp. 304-309.*

Y. Zhou, L. Hu, and G. Gruner. "A method of printing carbon nanotube thin films." Applied Physics Letters 88, 123109. (Mar. 22, 2006).*

K. Bradley, J-C. P. Gabriel, and G. Gruner. "Flexible Nanotube Electronics." Nano Letters. vol. 3, No. 10. pp. 1353-1355. (2003).*

J. Kong, M. G. Chapline, and H. Dai. "Functionalized Carbon Nanotubes for Molecular Hydrogen Sensors." Adv. Matter. 13, No. 18. pp. 1384-1386. (2001).*

(Continued)

*Primary Examiner*—Lisa M Caputo
*Assistant Examiner*—Punam Roy
(74) *Attorney, Agent, or Firm*—Thomas W. Tolpin; Tolpin & Partners, PC

(57) ABSTRACT

Single-walled carbon nanotubes (SWNTs) are decorated with metal nanoparticles to form high-performance flexible hydrogen sensors. The special process to form the high-performance flexible hydrogen sensors can combine a dry transfer printing technique and modification of SWNTs with palladium (Pd) nanoparticles to provide high-performance hydrogen sensors with excellent mechanical flexibility on plastic substrates. Two approaches can be used to decorate the SWNTs. One is physical deposition, such as electron beam evaporation (EBE) and the other is electrochemical deposition which can selectively grow palladium nanoparticles on the surface of the SWNTs, resulting in significantly decreasing the use of palladium. Preferably, the Pd nanoparticles are deposed on the SWNTs in a discontinuous arrangement so that the Pd nanoparticles are spaced away from each other to form individual discontinuous Pd nanoparticles rather a continuous Pd film. Advantageously, the SWNTs are arranged with substantial semiconducting pathways. Desirably, the high-performance flexible hydrogen sensors have an excellent response and recovery time, provide superior sensitivity for detecting hydrogen, and are bendable to conform to the contours of other structures.

9 Claims, 14 Drawing Sheets

OTHER PUBLICATIONS

Q. Cao, Z.-T. Zhu, M. G. Lemaitre, M.-G. Xia, M. Shim, and J. A. Rogers. "Transparent flexible organic thin-film transistors that use printed single-walled carbon nanotube electrodes." Applied Physics Letters 88, 113511.( Mar. 15, 2006).*

T. Takenobu et al. "High-performance transparent flexible transistors using carbon nanotube films." Applied Physics Letter 88, 033511. (Jan. 19, 2006).*

Publication: Yugang Sun, et al., "Electrodeposition of Pd Nanoparticles on Single-Walled Carbon Nanotubes for Flexible Hydrogen Sensors", Applied Physics Letters 90, American Institute of Physics, Illinois, 2007.

Publication: Yugan Sun, et al., "High-Performance, Flexible Hydrogen Sensors That Use Carbon Nanotubes Decorated with Palladium Nanopartiles", Advanced Materials, 2007, pp. 1-7.

* cited by examiner

FIG. 4 ns can be processed at relatively low temperatures (≦150° C.). This separation of high-temperature steps and low-temperature ones enables the fabrication of flexible thin-film transistors (TFTs) as well as other classes of devices on plastic sheets with the use of CVD SWNTs.

It is, therefore, desirable to provide a strategy for generating flexible hydrogen sensor, which overcomes most, if not all of the preceding disadvantages.

HIGH-PERFORMANCE FLEXIBLE HYDROGEN SENSORS

STATEMENT REGARDING FEDERALLY SPONSORED RESEARCH OR DEVELOPMENT

The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

BACKGROUND OF THE INVENTION

This invention relates to hydrogen sensors, and more particularly, to a high-performance flexible hydrogen sensor.

Hydrogen sensing is an important issue in a wide range of hydrogen related areas, such as industrial processing, fuel cells, hydrogen storage and hydrogen separation, etc. Traditional hydrogen sensors are usually fabricated with pure palladium (Pd) films on inorganic substrates, such as glass, quartz, silicon wafers, etc. The rigidity and/or fragility of these traditional hydrogen sensors associated with the use of rigid substrates might limit their applications in portable devices, transportation vehicles, aeronautic and civil engineering that require flexible, lightweight, and mechanic shock resistant sensing elements.

In contrast, thin polymer sheets with electrical and chemical inertness provide a useful class of substrates for fabricating hydrogen sensors. Typical designs of hydrogen sensors rely on the change in resistance of thin Pd films with continuous or discontinuous morphologies, as well as nanowires or nanotubes made of Pd upon exposure to hydrogen. These Pd micro- and nano-structures are generally not suitable for flexible design because their resistivities tend to change significantly due to the formation of cracks or change in gaps between individual Pd grains under bending deformation.

Another class of sensors depend on Schottky contacts formed between Pd films and semiconductors (e.g., GaAs, InP, Si, etc.), where the reaction between Pd and hydrogen (i.e. formation of palladium hydride) lowers the transport barrier through the contacts, thus increases current flow. These commercial field effect transistors (FET) sensors are usually fabricated on rigid semiconductor wafers.

It has recently been shown that individual single walled carbon nanotubes (SWNTs) as well as nanotube networks grown through chemical vapor deposition (CVD) had enhanced sensing capability for hydrogen when they were decorated or fabricated with palladium (Pd) via electron beam evaporation (EBE). Furthermore, solution-based SWNT films modified with palladium nanoparticles through chemical reactions and physical deposition, e.g. thermal evaporation and sputtering, can also serve as sensing elements for hydrogen detection. However, solution processed carbon nanotubes are limited by their performance in comparison to CVD carbon nanotubes. Therefore, CVD SWNTs modified with Pd nanoparticles provide a promising class of new materials for fabricating high-performance hydrogen sensing elements.

One problem is that the high temperature steps (~900° C.) involved in the growth of SWNTs, as well as thermal annealing for removing surfactants of solution SWNTs, are generally not compatible with flexible plastic substrates that can only withstand temperatures to ~300° C.

A dry transfer process has been developed for transferring CVD nanotubes onto plastic substrates where device fabrica-

BRIEF SUMMARY OF THE INVENTION

Improved hydrogen sensors are provided for high-performance hydrogen sensing. Advantageously, the high-performance hydrogen sensors are flexible and bendable so as to readily conform and complement the contours of other structures. Desirably, the high-performance hydrogen sensors have rapid response and recovery times and are economical, durable, attractive, and effective.

The inventive hydrogen sensors comprise devices providing detectors which provide high-performance flexible hydrogen sensor for sensing hydrogen. The high-performance flexible hydrogen sensors can comprise: (a) single-walled carbon nanotubes (SWNTs); (b) flexible plastic substrates for supporting the SWNTs; and (c) palladium (Pd) nanoparticles on the SWNTs positioned in an arrangement to provide a matrix in which Pd nanoparticles are spaced away from each other to form individual discontinuous Pd nanoparticles rather a continuous Pd film. Desirably, the high-performance sensors are flexible and bendable while substantially maintaining performance. The improved hydrogen sensors have enhanced sensitivity to hydrogen and quicker response and recovery times in comparison to traditional sensors. For better results, the SWNTs have substantial semiconducting pathways.

Preferably, the SWNTs and said Pd nanoparticles have densities and the sensors have dimensions which cooperate with each other to enhance sensing performance of said sensors. Desirably, the SWNTs having a greater ratio of channel lengths to channel widths for enhanced sensitivity to hydrogen.

In the preferred form, the plastic substrate comprises polyethylene terephtalate (PET) coated with a layer of epoxy resin. =In another form, arrays of high-performance flexible hydrogen sensors are provided for multiple point detection.

Advantageously, the hydrogen sensors have high-performance flexible sensing mechanisms for detecting hydrogen. Desirably, the flexible and bendable sensors are capable of conforming and being complementary to surfaces and contours of other structures while maintaining performance.

The inventive process for fabricating hydrogen sensors, comprises the steps of: (1) growing single-walled carbon nanotubes (SWNTs); (2) transferring the SWNTs on a substrate; (3) placing palladium (Pd) nanoparticles on the SWNTs in an discontinuous arrangement so that Pd nanoparticles are spaced away from each other to form individual discontinuous Pd nanoparticles rather a continuous Pd film; and (4) forming flexible and bendable high-performance hydrogen sensors. Desirably, the SWNTs are arranged with substantial semiconducting pathways. The SWNTs can be transferred on the substrate by dry transfer printing.

In an illustrative embodiment, a network of said SWNTs are grown on a wafer comprising silicon (Si) coated with silicon dioxide ($SiO_2$) and the substrate is formed of polyethylene terephtalate (PET) coated with epoxy resin. Electrodes can be attached to the sensors by thermal evaporation.

The palladium (Pd) nanoparticles can be placed on the SWNTs by high-vacuum evaporation comprising electron beam evaporation (EBE) or by electrochemical deposition comprising electrochemical reactions on the surfaces of the SWNTs.

One illustrated process comprises: (a) photolithographic patterning and deposition of a bilayer comprising chromium (Cr)/gold (Au) on a wafer followed by liftoff to form a meshed metal film providing an etching mask with an array of holes; (b) dissolution of a silicon dioxide ($SiO_2$) layer on the wafer to release the SWNTs; (c) the transferring comprising laminating an elastomeric polydimethylsiloxane (PDMS) stamp as a transfer element against the bilayer comprising chromium/gold and peeling off the PDMS stamp from the wafer to transfer the SWNTs to the PDMS stamp; (d) laminating the PDMS stamp on to a substrate formed of polyethylene terephtalate (PET) coated with epoxy resin; (e) heating the substrate to bond the SWNTs to the substrate; (f) peeling off the PDMS stamp; (g) dissolving the bilayer with a gold etchant and a chromium etchant; (h) forming semiconducting SWNTs on the substrate; and (i) depositing electrodes against a shadow mask to form flexible hydrogen sensors.

Advantageously, this invention can provide single-walled carbon nanotubes decorated or fabricated with metal nanoparticles for high-performance flexible hydrogen sensors. The invention can combine the dry transfer printing technique and modification of SWNTs with palladium (Pd) nanoparticles to prepare high performance hydrogen sensors with excellent mechanical flexibility on plastic substrates. Two approaches can be used to decorate or fabricate the SWNTs. One is physical deposition (electron beam evaporation, or EBE, and thermal evaporation) and the other is electrochemical deposition, which can selectively grow palladium nanoparticles on the surfaces of the SWNTs, resulting in significantly reducing the use of palladium.

The invention provided unexpected surprisingly good results. High-performance flexible hydrogen sensors, as well as sensory skins made of large-area arrays of high-performance flexible hydrogen sensors, can be useful where traditional sensors are not suitable. In particular, high-performance flexible hydrogen sensors can be beneficial to systems that require flexible, lightweight, and mechanical shock-resistant sensing elements. Furthermore, flexible hydrogen sensory skins comprising arrays of high-performance flexible hydrogen sensors can be useful for precisely monitoring hydrogen leakage of space shuttles which are driven or powered with hydrogen. Moreover, high-performance flexible hydrogen sensors can also benefit automobiles and other vehicles and portable devices which are driven or powered by hydrogen fuel cells and use of hydrogen storage tanks because of the exceptional properties of lightweight, high-performance, flexible hydrogen sensors. Also, high-performance flexible hydrogen sensors can provide "smart fabrics" in which the sensing elements can be part of a uniform for workers or military personnel under hazardous conditions. Still further, high-performance flexible hydrogen sensors can be useful in various systems which require light weight, mechanical flexibility, and/or high sensitivity.

A more detailed explanation of the invention is provided in the following detailed descriptions and appended claims taken in conjunction with the accompanying drawings.

BRIEF DESCRIPTION OF THE DRAWINGS

FIG. 2 (B) showing a schematic diagram of step (ii) illustrating the transfer printing of SWNTs, deposition of Ti/Pd electrodes and deposition of Pd clusters; and FIG. 2 (C) showing a schematic diagram of step (iii) illustrating bending and measuring resistance of a high-performance flexible hydrogen sensor in accordance with principles of the present invention.

FIG. 4 are charts illustrating the performance characterization of a high-performance flexible hydrogen sensor with channel length of 4.2 mm and width of 3.8 mm for sensing hydrogen molecules in air at room temperature, with FIG. 4 (a) illustrating variation of resistance as a function of time when the sensor was repeatedly exposed to 500 ppm hydrogen in air and to pure air.

FIG. 4(b) illustrating response curves of the high-performance flexible hydrogen sensor to hydrogen with different concentrations: 100, 200, 500, 1000, 2000, 5000 and 10000 ppm (from left to right).

FIG. 4 (c) illustrating the dependence of sensitivity and response time of the high-performance flexible hydrogen sensor on the concentration of hydrogen.

DETAILED DESCRIPTION OF THE INVENTION

The following is a detailed description and explanation of the preferred embodiments of the invention and best modes for practicing the invention.

Single-walled carbon nanotubes (SWNTs) on thin plastic substrates can be decorated, fabricated, integrated and interspersed with palladium (Pd) nanoparticles through an electrochemical deposition process and used to fabricate high-performance hydrogen sensors with excellent mechanical flexibility. The use of single-walled carbon nanotubes for sensing technology is attractive because interactions between target molecules and SWNTs can significantly change the electronic properties (e.g., capacitance, resistance, etc.) of SWNTs. Chemical sensors on the basis of change in resistance, also called chemiresistors, can be used to detect a wide range of species, such as nerve agents, explosives, environmental pollutants, and hydrogen, with high sensitivities. Hydrogen ($H_2$) represents an important energy carrier among these chemical species that has great potential in industrial processing, fuel cells, hydrogen storage and separation, aerospace transportation, etc. Therefore, development of sensitive hydrogen detectors (hydrogen sensors) is important to assure safety for economy, environment, and society. Modifying the surface of SWNTs with a layer of materials which could selectively concentrate and react with the target molecules can enhance the sensitivity of sensors fabricated with the SWNTS. Coating thin layers of Pd on SWNTs of both chemical vapor deposition (CVD) and solution processed types via various physical deposition techniques (e.g., electron-beam evaporation (EBE), sputtering, and thermal evaporation) can dramatically increase the sensing capability toward hydrogen molecules.

The use of high-vacuum evaporation instruments, however, increases the fabrication cost and the usage of palladium (Pd). Furthermore, deposited Pd atoms can form Pd nanoparticles with relatively wide size distribution on the surfaces of SWNTs as well as in the areas of the substrates uncovered with SWNTs. In the preferred process, as described hereinafter, however, a simple electrochemical approach is provided to selectively deposit uniform Pd nanoparticles only onto the surfaces of SWNTs on flexible plastic substrates, resulting in saving Pd and reducing fabrication and manufacturing costs. The hybrid SWNTs/Pd structures can serve as useful building blocks for fabricating hydrogen sensors with excellent sensing performance and mechanical flexibility, which is difficult to achieve for traditional hydrogen sensors constructed with pure Pd structures.

Figure 1:
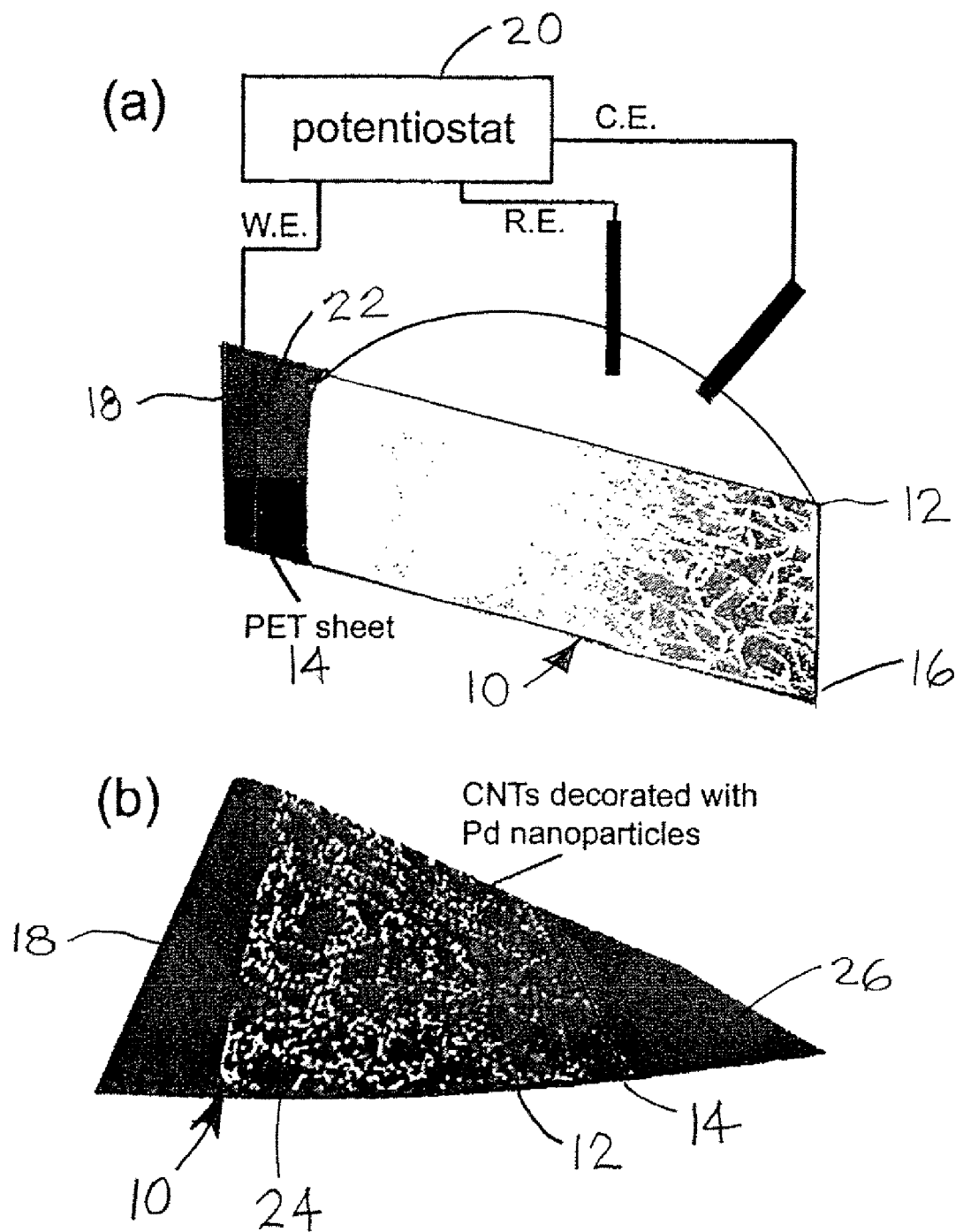
FIG. 1(a) is a diagram of a configuration used for electrochemical deposition of palladium (Pd) nanoparticles on the surfaces of single walled carbon nanotubes (SWNTs).
FIG. 1(b) is a diagrammatic front view of a high-performance flexible hydrogen sensor on a polyethylene terephtalate (PET) substrate with the use of modified SWNTs that is intentionally twisted in order to illustrate mechanical flexibility of the sensor in accordance with principles of the present invention.

As shown in FIG. 1, fabrication of high-performance flexible hydrogen sensors 10 can commence with growth of a network of high-quality single-walled carbon nanotubes (SWNTs) 12, also referred to as carbon nanotubes (CNTs) on a $SiO_2$/Si wafer through chemical vapor deposition (CVD). The as-grown SWNTs can then be transferred onto a plastic polyethylene terephtalate (PET) substrate 14 comprising a sheet (web), such as a thickness of approximately (~) 75 μm coated with a thin layer of epoxy resin 16 serving as an adhesive layer, such as with a thickness of ~2 μm with the use of an elastomeric polydimethylsiloxane (PDMS) stamp as a transfer element. Depositing a thin gold (Au) layer, such as 40 nm in thickness, on one end of a stripe of SWNT network can form an electrode 18 for connection to a potentiostat 20 [FIG. 1 (a)]. Overlaying partial area of the gold electrode with a layer 22 of silicon dioxide ($SiO_2$), such as ~60 nm in thickness, can prevent the deposition of palladium (Pd) onto the gold electrode during electrodeposition.

Placing a drop, such as ~0.5 ml, of an aqueous solution comprising 0.5 mM $Na_2PdCl_4$ and 100 mM $NH_4Cl$ on the PET sheet with SWNTs and connecting the reference electrode (RE) (Ag/AgCl in 3M NaCl solution), counter electrode (CE, Pt wire), and working electrode (WE) to the potentiostat according to configuration shown in FIG. 1 (a) enables generation and deposition of palladium (Pd) nanoparticles 24 on the surfaces of the SWNTs through reduction of $PdCl_4^{2-}$ anions. The potential applied to the gold electrode (WE) can be −1.0 V versus Ag/AgCl. The densities and sizes of the resulting Pd nanoparticles can be easily tuned by controlling the reaction time. Thereafter, the electrochemical reaction can be terminated, the electrolyte solution can be removed, the sample can be rinsed with water, and dried with nitrogen ($N_2$) stream to finish decoration of the SWNTs with Pd nanoparticles. In the next step, the $SiO_2$ layer can be dissolved followed by depositing two gold electrodes 18 and 26 [one of them overlaid the gold layer in FIG. 1 (a)] with the use of thermal evaporation against a shadow mask to complete the fabrication of a mechanically flexible hydrogen sensing device on the PET substrate [FIG. 1 (b)].

A flexible hydrogen sensor fabricated through the aforementioned procedure can be bended and the SWNTs decorated with Pd nanoparticles can be almost transparent. The transparence is attributed to the absorption of the SWNTs in near infrared regime and the low absorption of Pd nanoparticles due to their small sizes and low coverage. The Pd nanoparticles can be deposited by applying four pulses of 1 s (second) long constant potential of −1 V versus Ag/AgCl. An atomic force microscopy (AFM) micrograph of the Pd nanoparticles on the SWNTs shows the formation of individual Pd nanoparticles with sizes ranging from 20-50 nm and a necklace like arrangement. The results indicated that only the surfaces of the SWNTs were coated with Pd nanoparticles and most of the adjacent Pd nanoparticles were separated with gaps. The selective deposition of Pd on the surface of the SWNTs can significantly reduce the usage of expensive Pd compared with physical evaporation methods used in traditional fabrication. Furthermore, the discontinuity of the Pd nanoparticles formed under short electrodeposition time ensured that the resistance between the two gold electrodes was determined by the semiconducting SWNT network. The Pd nanoparticles can increase the interaction between $H_2$ and SWNTs to enhance the change of resistance of the device when it was exposed to hydrogen molecules. The as-fabricated hydrogen sensor can be systematically characterized by sealing it in a small chamber which can be flushed with hydrogen gas diluted by air, such as with a total flow rate of ~1300 sccm. The flexible hydrogen sensor can be cut into narrow stripes to produce a number of hydrogen sensors with different widths, resulting in further decreasing fabrication cost.

Figure 4:
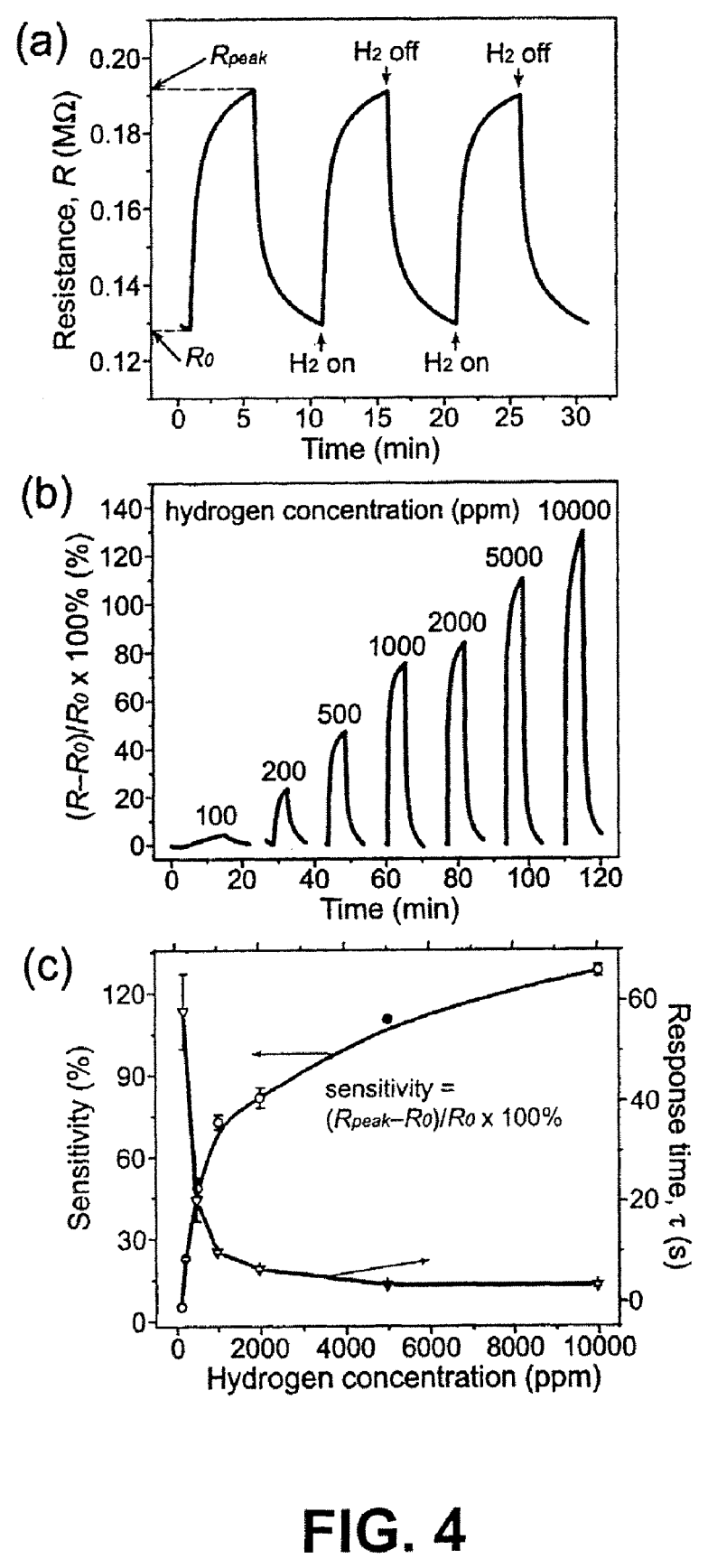

FIG. 4a presents a chart that illustrates the variation of resistance of a typical sensor when the hydrogen flow with concentration of 500 ppm was turned on and off for three cycles at room temperature (~22° C.). This sensor had channel length (i.e., the distance between the two gold electrodes) of 4.2 mm and channel width (i.e., the width of the SWNT network) of 3.8 mm. This curve shows that for each cycle the resistance increased quickly once the device was exposed to hydrogen and the resistance increase became slow at longer exposure time. The resistance essentially returned to the original value after the hydrogen flow was shut off and the chamber was flushed with pure dry air for 5 min, indicating the easy recovery of the as-fabricated sensors. The sensing behavior of the as-fabricated device is similar to that of hydrogen sensors fabricated with SWNTs modified with Pd films through physical depositions on rigid substrates. When the hydrogen sensor (device) was exposed to hydrogen, the Pd nanoparticles quickly reacted with hydrogen to form palladium hydride (PdHx) that possessed lower work function than pure Pd. The lower work function associated with PdHx was beneficial to the transfer of more electrons from Pd nanoparticles to SWNTs to trap the p-type carriers in the SWNTs, resulting in an increase of resistance of the SWNT network. The conversion percentage of Pd (to PdHx) increased with increasing concentration of hydrogen, thus increased the maximum change of resistance of the sensor.

The chart of FIG. 4b compares the responses of the hydrogen sensor when it was exposed to the atmospheres containing hydrogen of different concentrations. A notable resistance change of ~5% was observed even for the sample with hydrogen concentration of as low as 100 ppm. The ratio between the maximum change of resistance and the resistance measured in pure air, i.e., $(R_{peak}-Ro)/Ro \times 100\%$, is usually referred to as sensitivity to evaluate the performance of hydrogen sensors. $R_{peak}$ and Ro represent the maximum resistance recorded after the sensor was exposed to hydrogen and the resistance measured in pure air, respectively, and are illustrated in FIG. 4a.

The chart of FIG. 4c plots the sensitivities extracted from FIG. 4b as a function of the hydrogen concentration, indicating that the sensor on plastic substrate had comparable sensitivities to sensors fabricated with SWNTs on rigid substrates, and much higher sensitivities than those fabricated with pure Pd materials. Response time τ defined as the time required for the sensor to reach $e^{-1}$ (i.e., ~36.8%) of the maximum resistance change after the sensor is exposed to a given gas, represents another important parameter of hydrogen sensor. FIG. 4c also plots the dependence of response time and the concentration of hydrogen, indicating that higher concentration of hydrogen resulted in a faster response. For example, the response time was as short as ~3 s when the sensor was exposed to 1% hydrogen in air.

Figure 5:
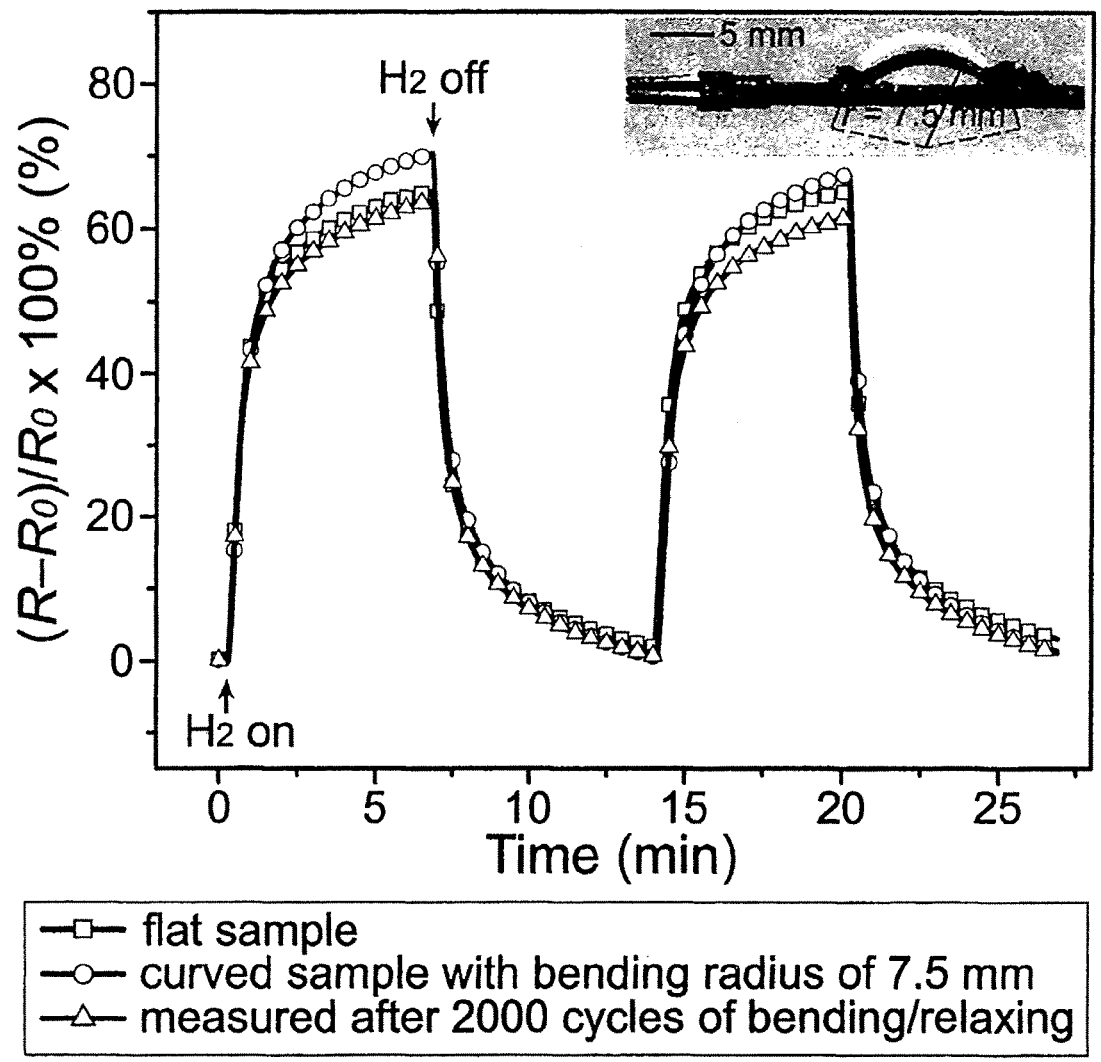
FIG. 5 is a chart illustrating bending and fatigue tests over a high-performance flexible hydrogen sensor when the high-performance flexible hydrogen sensor was exposed to 500 ppm hydrogen in air. The inset in the chart presents the optical image of the high-performance flexible hydrogen sensor with curved geometry mounted on a probe holder.

Mechanical bendability of the as-fabricated sensors represents an important parameter for applications that are difficult or impossible to achieve with traditional sensors on rigid substrates. FIG. 5 compares the responses of a flexible sensor to 500 ppm (i.e., 0.05%) hydrogen in air when it was laminated on a flat surface (trace with squares) and was bended into curved profile (as shown in the inset) with bending radius of ~7.5 mm (trace with circles). The minor difference between the two characteristic traces indicates that bending the sensor did not affect its sensing performance significantly, i.e., no change in response time and a slight increase less than 5%) in sensitivity. Fatigue test (trace with triangles in FIG. 5) shows that there was essentially no degradation in performance even after the sensor was squeezed to a curved profile (with bending radius of ~7.5 mm) followed by relaxing to flat geometry for 2000 cycles. These results indicated that the flexible hydrogen sensors on PET substrates exhibited excellent mechanical bendability and durability.

The variation of resistance of a hydrogen sensor when the hydrogen flow was turned on and off, such as for three cycles at room temperature provided the following. For each cycle the resistance increased quickly once the hydrogen sensor was exposed to hydrogen and the increase rate of resistance became slow at longer exposure time. The resistance generally returns to the original value after the hydrogen flow is shut off and the chamber is flushed with pure dry air for a sufficient time to indicate recovery of the as-fabricated sensor. The sensing behavior of the as-fabricated hydrogen sensor can be similar to that of hydrogen sensors fabricated with SWNTs modified with Pd films through physical depositions on rigid substrates.

When the hydrogen sensor was exposed to hydrogen, the Pd nanoparticles quickly reacted with hydrogen to form palladium hydride (PdHx) that possessed lower work function than pure Pd. The lower work function associated with $PdH_x$ is beneficial to the transfer of more electrons from Pd nanoparticles to SWNTs to trap the p-type carriers in the SWNTs, resulting in an increase of resistance of the SWNT network. The SWNTs can play a role of transducer and amplifier to convert the chemical reactions between Pd and hydrogen into strong electrical signals. The conversion percentage of Pd (to $PdH_x$) increases with increasing concentration of hydrogen to increase the maximum change of resistance of the sensor. When the hydrogen sensor was exposed to the atmospheres containing hydrogen of different concentrations, a notable resistance change of ~5% was observed even for the gas with hydrogen concentration of as low as ~100 ppm. The ratio between the maximum change of resistance and the resistance measured in pure air is usually referred to as sensitivity to evaluate the performance of hydrogen sensors. The hydrogen sensor on plastic substrate had comparable sensitivities to the sensors fabricated with SWNTs on rigid substrates and much higher sensitivities than those fabricated with pure Pd materials. The coverage of Pd nanoparticles on the surfaces of the SWNTs, which can be easily controlled by the electrodeposition time, significantly affected the sensitivities of the sensors. Higher concentration of hydrogen also provides a faster response.

Mechanical bendability of the as-fabricated sensors represents an important parameter for applications that are difficult or impossible to achieve with traditional sensors on rigid substrates. Bending the high-performance flexible hydrogen sensor did not affect its sensing performance significantly, i.e., no change in response time and a slight increase in sensitivity. A fatigue test indicated that there was essentially no degradation in performance even after the sensor was squeezed to a curved profile, such as with bending radius of ~7.5 mm, followed by relaxing to a flat (planar) geometry, such as for 2000 cycles. These results indicated that the sensors on PET substrates exhibit excellent mechanical bendability and durability.

As indicated previously, the surfaces of SWNTs on PET substrates can be decorated or fabricated with Pd nanoparticles via a simple electrochemical deposition process. The resulting composite nanostructures provide active building blocks for the fabrication of mechanically flexible hydrogen sensors. The characteristics of the as-fabricated flexible hydrogen sensors suggest they can be useful for fast and sensitive detection under conditions such as conformal wrapping over curvilinear surfaces, high tolerance toward repeated bending, and mechanical shock resistance.

The inventive high-performance flexible hydrogen sensors with the SWNTs decorated with EBE Pd nanoparticles and Ti/Pd electrodes provided unexpected surprisingly good results. The sensitivity (i.e., change of resistance) of the high-performance flexible hydrogen sensors were generally at ~100% for 0.1% (volume/volume) hydrogen in air at room temperature. Response times were typically around 1.5 s (seconds) for 1% hydrogen and the high-performance flexible hydrogen sensors were generally completely recovered within one (1) minute. Significantly, the high-performance flexible hydrogen sensors could detect hydrogen in concentrations as low as 30 ppm (0.003%). Experimental results indicated the as-fabricated devices operated well even when bent to a curved geometry, such as with a bending radius down to 2 mm. Furthermore, fatigue tests showed that the high-performance flexible hydrogen sensors had good durability.

Figure 2:
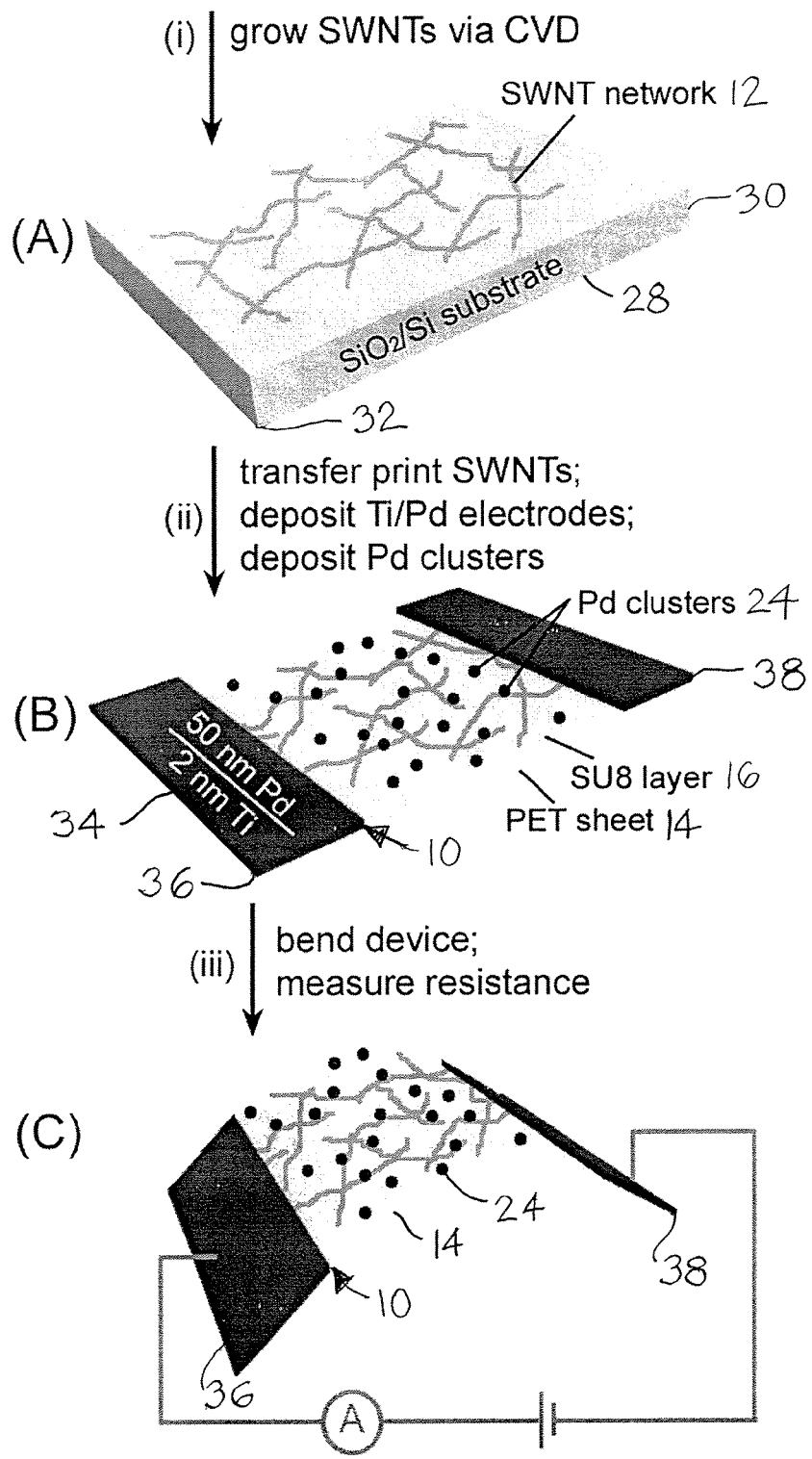
FIG. 2 is schematic flow diagram of a process for fabricating flexible high-performance hydrogen sensors with a film of SWNTs decorated with Pd nanoclusters on a plastic PET/epoxy resin substrate in accordance with principles of the present invention with FIG. 2 (A) showing a schematic diagram of step (i) illustrating the growing of SWNTs by chemical vapor deposition (CVD)

FIG. 2 schematically depicts the major steps involved in the fabrication of high-performance flexible hydrogen sensors 10 with SWNTs 12 decorated with Pd nanoclusters 24. The fabrication can commence with the growth of a high-quality SWNT film through chemical vapor deposition (CVD) on a substrate 28, such as a silicon (Si) wafer 30 covered with a layer 32 of silicon dioxide ($SiO_2$), such as a 100 nm $SiO_2$ layer, that had been cleaned with a cleaning solution, such as a piranha solution (step i). The cleaning step can remove all organic contaminations and convert the wafer surfaces to be hydrophilic. Typical SWNT films can have a density of ~14 tubes/$\mu m^2$ and individual nanotubes can have diameters ranging from 1 to 2 nm. In the next step (step ii), the as-grown nanotube network as shown in FIG. 2A, was transfer printed onto a poly(ethylene terephtalate) (PET) substrate 14 (sheet), such as at a thickness of ~75 μm, covered with a thin layer 16 of epoxy resin with assistance of an elastomeric polydimethylsiloxane (PDMS) stamp as the transfer tool. The epoxy resin layer, such as at a thickness of ~2 μm, can be important not only to facilitate the transfer printing process, but also to prevent the SWNTs from flaking away from the PET substrate. Deposition of metal bilayers 34, such as 2 nm Ti/50 nm Pd bilayers, over the SWNT film against a shadow mask can form electrodes 36 and 38. Thereafter, deposition, such as flood deposition, of another thin palladium (Pd) film, such as with thickness ranging from 5 to 30 Å, preferably via an electron beam evaporation (EBE), such as with a base pressure of 1.5×10−6 Torr, can finish the fabrication of a high-performance flexible hydrogen sensor 10, such as shown in FIG. 2 (B). Instead of formation of continuous Pd film, the evaporated Pd atoms in the second deposition nucleate and desirably grow into individual Pd nanoparticles, some of which attach on the surface of SWNTs to serve as hydrogen sensing elements while some other Pd nanoparticles dispersed in the areas absent of nanotubes. The density and size of the Pd nanoparticles can be tuned by controlling the thickness of the evaporated Pd. The Pd nanoparticles on SWNTs determine the performance of the as-fabricated hydrogen sensor. Hydrogen molecules can be detected by monitoring the change of resistance between the two Ti/Pd electrodes when the high-performance hydrogen sensor was exposed to hydrogen. The excellent mechanical properties of SWNTs and flexibility of the thin PET/epoxy resin sheet (substrate) helped the high-performance flexible hydrogen sensor to work well even when bent, as shown in FIG. 2 (C).

The high-performance flexible hydrogen sensor, has excellent hydrogen sensing capabilities, and is desirably flexible. The sensor can be coated such as with a 5 Å palladium (Pd) film to modify the surface of SWNTs. The resistance of the SWNT film between the two Ti/Pd electrodes i.e., channel region, in one example increased by ~24.5% after the Pd modification. The change in resistance indicates that the evaporated Pd atoms formed individual (discontinuous) Pd nanoparticles rather than a continuous film because a continuous Pd film can undesirably significantly increase the conductivity of the sensor. Palladium (Pd) is metallic and much more conductive than the semi-conductive SWNTs. Furthermore, a Pd film, such as with a thickness of 15 Å deposited on a PET substrate but without SWNTs was not conductive, further con-firming the discontinuity of the Pd film. As indicated previously, the hydrogen sensors can have a necklace-like structures formed with individual Pd nanoparticles, such as with sizes less than 5 nm, assembled along the surfaces of the SWNTs. Palladium (Pd) atoms, however, formed many relatively large nanoparticles in the regions without SWNTs. The non-uniformity in size of the Pd nanoparticles can be ascribed to the surface roughness of the SU8/PET substrate. Close observation of the sensor revealed the discontinuity of the Pd nanoparticles on the SWNTs. The gaps between individual nanoparticles were clearly shown in the phase mode atomic force microscope (AFM) image.

Advantageously, the as-fabricated sensor (device) can be easily cut into a number of sensors with desired widths for different applications. These fabrication techniques and process can significantly reduce the fabrication cost per sensor.

In another example, a hydrogen sensor was fabricated with a channel length (L) of 6.5 mm and width (W) of 3.5 mm, and sealed in a small chamber which was flowed with hydrogen gas diluted by air with a total flow rate of ~1300 sccm. The two electrodes were connected to a computer-controlled Keithley 2001 digital multimeter via a BNC connector and a standard probe holder. The testing gases were formulated by mixing diluted hydrogen gas in argon (4.11% in volume) and compressed air. The final concentrations of hydrogen were tuned by controlling the flow rates of the two gases via MKS mass flow controllers. All measurements were carried out at room temperature (i.e., 22° C.). The results showed that the resistance of the hydrogen sensor quickly increased (by 53.3%) when the sensor was exposed to hydrogen with concentration of 0.1% (i.e., 1000 ppm) and the resistance decreased and essentially returned to the original value after the chamber was absent of hydrogen and flushed with air for ~2 min.

The performance of sensors for hydrogen sensing is usually evaluated by sensitivity and response time. Sensitivity can be defined by the percentage of the maximum resistance change for a gas with a fixed concentration of hydrogen:

$$\text{Sensitivity} = (R_{peak} - Ro)/Ro \times 100\%$$

Where Ro is the resistance of the sensor exposed to air only and $R_{peak}$ represents the highest resistance after exposure to a gas containing hydrogen. Response time, t, is defined as the time required for the sensor to reach $e^{-1}$ (i.e. ~36.5%) of the maximum resistance change after the sensor is exposed to a given gas. The responses can be recorded for the sensor in the environments with hydrogen at different concentrations. The results showed that exposure of the sensor to a higher concentration of hydrogen induced faster increase of the resistance to a higher peak value. A detectable resistance change of ~3% was achieved even for the sample with hydrogen concentration of as low as ~30 ppm. Significantly, the sensitivity of the sensor is nearly one order of magnitude better than Pd nanotube sensors, and also much better than sensors made from solution processed SWNTs on alumina or glass substrates. When hydrogen molecules react with Pd, the variation of work function of the Pd nanoparticles can be proportional to the fraction of the surface that is covered by hydrogen and linearly affects the effective concentration of p-type carriers in the SWNTs film.

The high-performance flexible hydrogen sensors on plastic substrates also exhibit shorter response times than the solution-based SWNT sensors. The sensing kinetics of the high-performance flexible hydrogen sensors can rely on the hydrogen dissociation process over palladium. The sensitivity of the SWNTs/Pd sensor (hydrogen sensors) can increase to 407% when measured in argon with 200 ppm hydrogen, while the response time lengthened to 320 s. The difference between the results collected from the atmospheres of air and argon (containing hydrogen of same concentrations) indicated that oxygen molecules compete with hydrogen molecules to react with Pd nanoparticles.

Sensitivities of the flexible sensors can also depended on the density of palladium (Pd) nanoparticles (i.e., the thickness of the deposited Pd films) on the SWNTs. The hydrogen sensors with thicker Pd films exhibit higher sensitivities when the thicknesses of the Pd films were less than 30 Å. Pd films with thicknesses of >5 nm can become conductive, leading to a failure in sensing mechanism. Furthermore, in addition to the thickness of Pd films, the density of SWNTs can significantly affect the performance of the resulting sensors. For example, the sensor fabricated with a high-density SWNT network, whose conductivity was mainly dominated by metallic pathways, exhibit much lower sensitivities than the sensors fabricated with moderate-density SWNT networks, whose conductivities were determined by semiconducting pathways. Flexible hydrogen sensors fabricated as described previously, are very stable toward the ambient environment. Desirably, the performance of a high-performance hydrogen sensor measured after fabrication was essentially the same as that measured after the sensor was stored for about 6 months in air. The performance of such flexible hydrogen sensors is also dependent on the ratio (L/W) between their channel lengths and widths when the density of SWNT networks and the thickness of Pd films were fixed. Sensitivities of the sensors systematically increased with increase of the ratio of L/W. These results indicated that the performance of flexible sensors can be determined by controlling the channel length, channel width, density of SWNTs and thickness of Pd film.

Mechanical flexibility of the as-fabricated sensors can be more important for practical applications that traditional sensors on rigid substrates cannot achieve. In a further example, the responses of a flexible sensor to 0.1% hydrogen in air when it was laminated on a flat (square) surface and on a cylindrical surface with radius of ~2 mm (circle) did not change significantly. The results showed that bending the high-performance flexible hydrogen sensor did not significantly adversely affect its sensing performance, i.e., no change in response time and a slight decrease (by 4.7%) in sensitivity. Even after the sensor was compressed to a curved surface (with bending radius of 2 mm) followed by relaxing to flat geometry for 1000 cycles at a rate of 100 cycles per min, its sensitivity decreased by only 13% and the response time did not change. These results indicate that the high-performance flexible hydrogen sensors on PET substrates exhibited excellent mechanically bendability and durability.

The inventive high-performance flexible hydrogen sensors provided unexpected surprisingly good results. From the preceding, it can be seen that flexible SWNTs/Pd hydrogen sensors with high sensing performance for ambient temperature applications can be beneficially fabricated by using electronic-quality semiconducting SWNT films decorated, fabricated, integrated and interspersed with small Pd nanoparticles on PET substrates. The inventive high-performance flexible hydrogen sensors had sensitivities much higher than traditional sensors fabricated with pure Pd materials on rigid substrates. The flexible sensors can detect hydrogen with concentrations as low as 30 ppm in air at room temperature. The high-performance flexible hydrogen sensors also exhibit fast response behaviors and short recovery times when they were operated in air. Also, the sensing performance of the novel high-performance flexible hydrogen sensors did not significantly degrade even when they were laminated on curved surfaces with radius as small as 2 mm and/or after they underwent 1000 times of bending/relaxing cycles. These results indicate that the high-performance flexible hydrogen sensors are very useful for applications in areas requiring light weight, conformal wrapping on curvilinear surfaces, mechanical shock resistance, and fast and sensitive detection. Furthermore, the material cost for the SWNTs/Pd sensors providing the high-performance hydrogen sensors can be significantly less than those made of pure Pd films or Pd nanotubes or Pd wires or Pd beads.

Accordingly, it has been shown that inventive high-performance hydrogen sensors with excellent mechanical flexibility and durability can be fabricated on thin plastic sheets with the use of high-quality semiconducting single-walled carbon nanotubes decorated with discrete Pd nanoparticles. These inventive sensors exhibit sensing performance much higher than the traditional ones built with precious pure palladium structures on rigid substrates. For example, the sensitivity of the typical flexible sensors can be the range of 100~150% (based on resistance change of the sensors) for 0.1% hydrogen in dry air at room temperature. The response times can be typically less than 15 s (seconds) for 1% hydrogen and the sensors can be completely recovered within 5 min in the air without hydrogen at ambient temperature. The flexible hydrogen sensors can detect hydrogen with concentrations as low as 100 ppm (0.01%). Desirably, the as-fabricated devices (flexible hydrogen sensors) operate well even when they are bent to a curved geometry with a bending radius down to 2 mm and after they are treated with 1000 times of bending/relaxing cycles.

SWNT films can be grown on silicon (Si) wafers covered with 100-nm thermally grown silicon dioxide ($SiO_2$) layers, and cleaned with a cleaning solution, such as a piranha solution ($H_2SO_4$ (98%):$H_2O_2$ (30%)=3:1 in volume), which can be heated, such as at 70° C. for 10 min. The cleaning process can remove all organic contaminations and can convert the wafer surfaces to be hydrophilic. In the next step, an appropriate amount of a catalyst precursor, such as an aqueous ferritin solution diluted by 20 times with deionized water can be delivered onto the $SiO_2$ surface of the cleaned wafer to wet the surface for about 30 s (seconds). Methanol can be slowly added to the ferritin solution to precipitate ferritin onto wafer surface for 30 s. The wafer can then be rinsed with methanol and dried, such as with nitrogen ($N_2$) flow. Heating the wafer with ferritin catalyst, such as at 800° C. in air and reducing them with $H_2$ flow, such as at 900° C., can transform the catalyst into a submonolayer of well-dispersed iron nanoparticles with diameters, such as ranging from 1 to 2 nm, which can catalyze the growth of SWNTs. The coverage of SWNTs can be tuned by controlling the concentration of ferritin catalyst and/or growth time. Methane ($CH_4$), such as at a flow rate of 2500 sccm and diluted with hydrogen $H_2$ (70 sccm) can serve as a precursor for the formation of carbon nanotubes at 900° C. The SWNT films grown by this procedure were dominated by semiconducting pathways and can be characterized as semiconducting SWNTs. Alternatively, SWNT films dominated by metallic pathways, also called metallic SWNTs, can be grown by using catalysts generated from a solution containing iron acetate (e.g. 6 mg,), cobalt acetate (e.g. 9 mg), molybdenum acetate dimer (e.g. 1.5 mg), and 40 mL ethanol suspension of silica (e.g. 100 mg). Spin casting the solution, such as at 3000 rpm for 1 min followed by reducing with hydrogen ($H_2$) flow at 2400 sccm and 840° C. and heating a mixture of $CH_4$ (2350 sccm) and $H_2$ (70 sccm) for 20 min at 840° C. can also generate metallic SWNTs.

Figure 3:
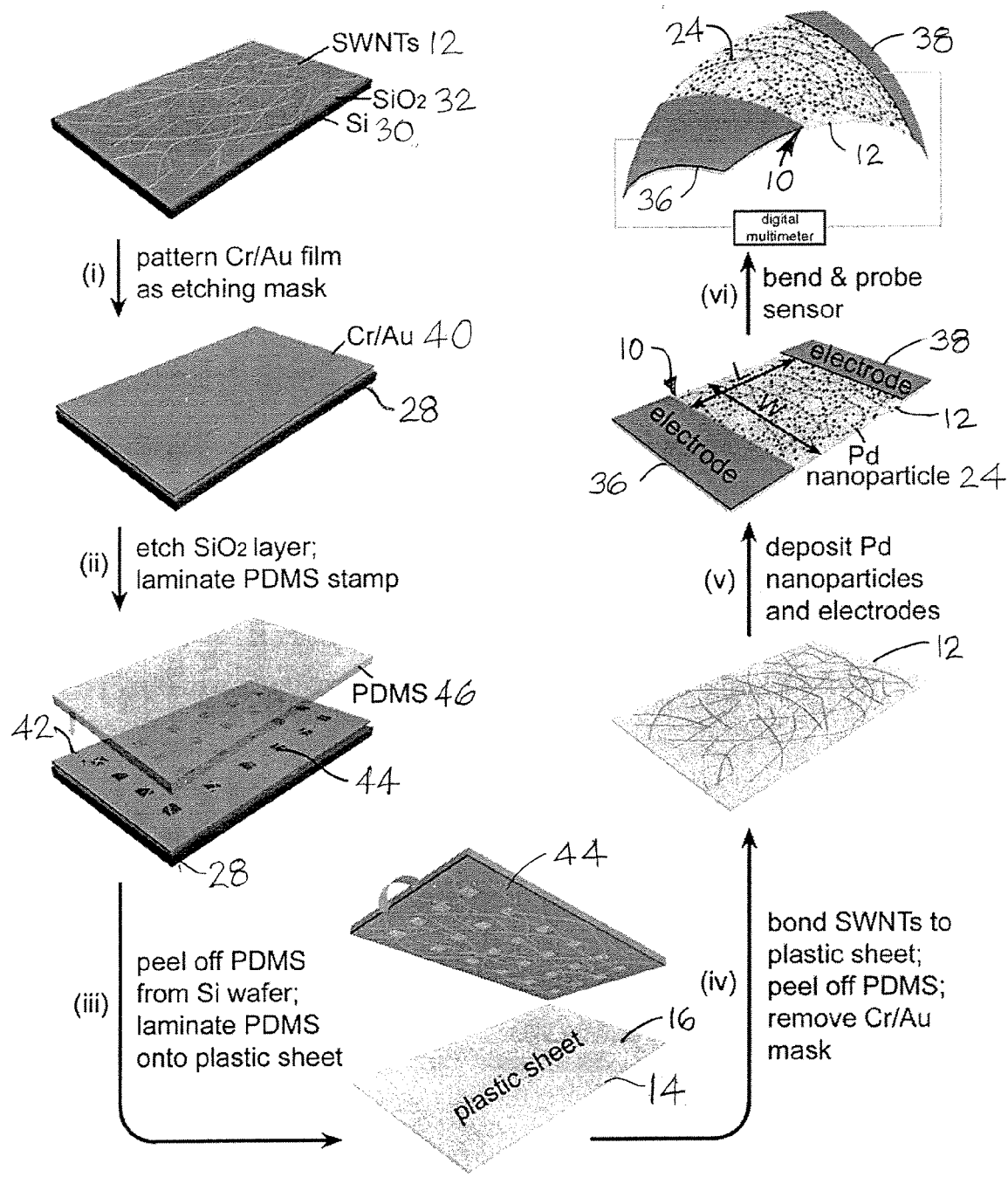
FIG. 3 is schematic flow diagram of a process for fabricating flexible high-performance hydrogen sensors on plastic substrates with a network of SWNTs dec-orated with Pd nanoparticles in accordance with principles of the present invention.

The fabrication of high-performance flexible hydrogen sensors can also be described with respect to FIG. 3. The major steps involved in the fabrication of a flexible hydrogen sensor can include transfer printing of a semiconducting SWNT film onto a plastic substrate and depositing of metal layers via electron-beam evaporation (EBE). FIG. 3 schematically illustrates the details of the procedure, which starts with the growth of network of high-quality semiconducting SWNTs 12 on a $SiO_2$/Si wafer 32 via chemical vapor deposition (CVD) described in the previous paragraph. Photolithographic patterning and deposition of a bilayer 40 chromium (Cr) (e.g. 10 nm)/gold (Au) (e.g. 50 nm) on the growth wafer 28 followed by liftoff can generates a metal film 42 with an array of square holes 44 (with edge length of ~5 μm). The meshed metal film can serve as an etching mask to remove the silicon dioxide ($SiO_2$) layer underneath the film of SWNTs because the square holes provide the access for aqueous hydrofluoric acid (HF) solution. Dissolution of the $SiO_2$ layer helps release the SWNTs from the growth substrate (step ii). The Cr/Au film also helps to prevent the SWNTs films from folding and cracking during etching. Laminating a flat elastomeric polydimethylsiloxane (PDMS) stamp 46 against the Cr/Au film forms conformal contact between the PDMS and the metal film due to the action of generalized adhesion forces (step ii). Peeling off the PDMS stamp back from the Si wafer transfers the SWNTs and the Cr/Au film to the PDMS stamp (step iii). Laminating the PDMS stamp onto a plastic substrate 14 (sheet) comprising a PET sheet (e.g. with thickness of ~75 μm) covered with a thin layer 16 of partially cured epoxy resin (SU8) (e.g. with thickness of ~2 μtm) followed by heating the system, such as for 10 min at 70° C., forms bonding between the nanotubes and the PET sheet (step iii). Peeling off the PDMS stamp and dissolving the Cr/Au layer with gold etchant (KI/$I_3^-$ aqueous solution) and chrome etchant (e.g. CRIA, Union Etchants International, Inc., Woburn, Mass.) can leave the semiconducting SWNTs on the plastic substrate (step iv). This process can transfer the SWNTs from the growth substrates with high yield approaching 100%. The nanotubes on the PET substrate can be further processed at temperatures lower than 150° C. with addition of other active components for functional devices. For example, depositing a very thin layer with thickness of less than 3 nm of Pd film via electron-beam evaporation (EBE) at room temperature leads to the decoration of the surfaces of the SWNTs with discrete Pd nanoparticles. Depositing two Ti/Au or Ti/Pd probing electrodes 36 and 38 against a shadow mask in the electron-beam evaporator can complete the fabrication of a flexible hydrogen sensor (step v). The channel length, L, (i.e., the distance between the two probing electrodes) and the channel width, W, (i.e., the width of the stripe of the SWNT film) can be readily tuned by using different shadow masks. The as-fabricated high performance hydrogen sensor is mechanically flexible and can be bent into curved profile (step vi). In this geometry, the Pd nanoparticles-decorated SWNTs in the channel region provide an important feature for sensing hydrogen molecules.

Resistance of high-performance flexible hydrogen sensors quickly increases e.g. by ~3 times when the high-performance flexible sensors are exposed to hydrogen molecules with concentration of 0.5% (i.e., 5000 ppm) in dry air at room temperature. When hydrogen is absence around the sensor, e.g., the sensor is surrounded with pure dry air, the resistance of the sensor drops and essentially returns to its original value. The results indicate that the as-fabricated high-performance hydrogen sensors can be easily recovered within short time span, e.g. less than 5 min.

FIG. 6A illustrates presents a typical hydrogen sensor (with Ti/Au probing electrodes) conformably laminated on the wall of a vial, clearly showing its mechanical flexibility. This sensor can be easily cut into multiple sensors with narrow channel widths, leading to further decrease in fabrication cost per sensor. FIG. 6B shows such a flexible hydrogen sensor generated from that shown in FIG. 6A and mounted to a probe holder with graphene paste (black scab). With assistance of photolithographic patterning, sensors with channel lengths and widths smaller than those shown in FIGS. 6A and 6B can also be fabricated. FIG. 6C shows a bent PET sheet with an array of hydrogen sensors, which can be used for detecting multiple spots simultaneously. The channel regions of this kind of sensors are highly transparent because of the absorption of the SWNTs in the near infrared regime and the small sizes and low coverage of the Pd nanoparticles. FIG. 6D presents a typical AFM image of the channel region, showing the formation of necklace-like structures. The results indicate that the SWNTs are decorated with individual Pd nanoparticles (formed from 1.5-nm thick Pd film) rather than continuous thin Pd films. A Pd film with thickness of 1.5 nm deposited on a bare PET substrate (without SWNTs) same as that used for the sensors is not conductive, further confirming the discontinuity of the Pd film. As a result, the charges still transport through the network of semiconducting SWNTs when the sensors are operated with biases.

In evaluating the performance of the flexible hydrogen sensors, the as-fabricated hydrogen sensors can be characterized by recording their resistance change when they are exposed to environments with hydrogen molecules of different concentrations. All the sensors illustrated were characterized at room temperature (~22° C.). FIG. 7A shows the variation of resistance of a sensor with channel length (L) of 4.4 mm and channel width (W) of 6.6 mm when the hydrogen flow is turned on and off for two cycles. The semiconducting SWNTs of this hydrogen sensor (device) were modified by depositing 1.5 nm Pd film and the concentration of hydrogen in this measurement is 0.5% (i.e., 5000 ppm) in dry air. It is measured when the hydrogen sensor is laminated on the flat surface of a probe holder (FIG. 6B). The typical curve obtained from this sensor shows that its resistance quickly increases by ~3 times (from 3.4 to 13.4 MΩ) when the flexible hydrogen sensor (device) was exposed to hydrogen molecules. When hydrogen is absence around the sensor, i.e., the sensor is surrounded with pure dry air, its resistance drops and essentially returns to its original value. The results indicate that the as-fabricated hydrogen sensors can be easily recovered within short time span, i.e., less than 5 min.

In general, a hydrogen sensor exhibits higher responses (i.e., higher sensitivities) when it is exposed to hydrogen with higher concentrations. The chart of FIG. 7B plots the response curves of the hydrogen sensor in the environments with hydrogen of different concentrations. This high-performance flexible hydrogen sensor can even detect hydrogen molecules of concentration as low as 0.01% with an observable signal, i.e., 2% in sensitivity (inset of FIG. 7B). The curves of FIG. 7B plot the relationship between the percentage of resistance change (rather than actual resistance) and time. This treatment leads to conveniently compare different devices with different geometrical dimensions and different Ro. The chart of FIG. 7B also show that the resistance of the sensor increases faster to a higher peak value upon exposure to hydrogen with a higher concentration. The sensitivities of the as-fabricated sensors made from semiconducting SWNTs decorated with Pd nanoparticles (SWNTs/Pd) on plastic substrates are higher than sensors made from SWNTs/Pd on alumina or glass substrates, and are at least one order of magnitude higher than sensors using pure Pd structures. The sensitivities of the sensor for hydrogen at different concentrations are plotted in FIG. 7C and FIG. 3D (traces with squares) against the actual concentration and square root of concentration of hydrogen, respectively. The linear correlation between the sensitivity and the square root of hydrogen concentration might be related to the dissociation process of hydrogen molecules on the surface of Pd nanoparticles according to the Langmuir adsorption isotherm theory. The reciprocal of the response time which is proportional to the reaction rate, has a linear correlation to the concentration of hydrogen (trace with squares in FIG. 8). The sensing performance of flexible hydrogen sensors fabricated can be influenced by various parameters. Therefore, systematical evaluation of the effects of processing and device geometries on sensing behavior of the devices is beneficial to fabricating optimized sensors with high performance.

Figure 9:
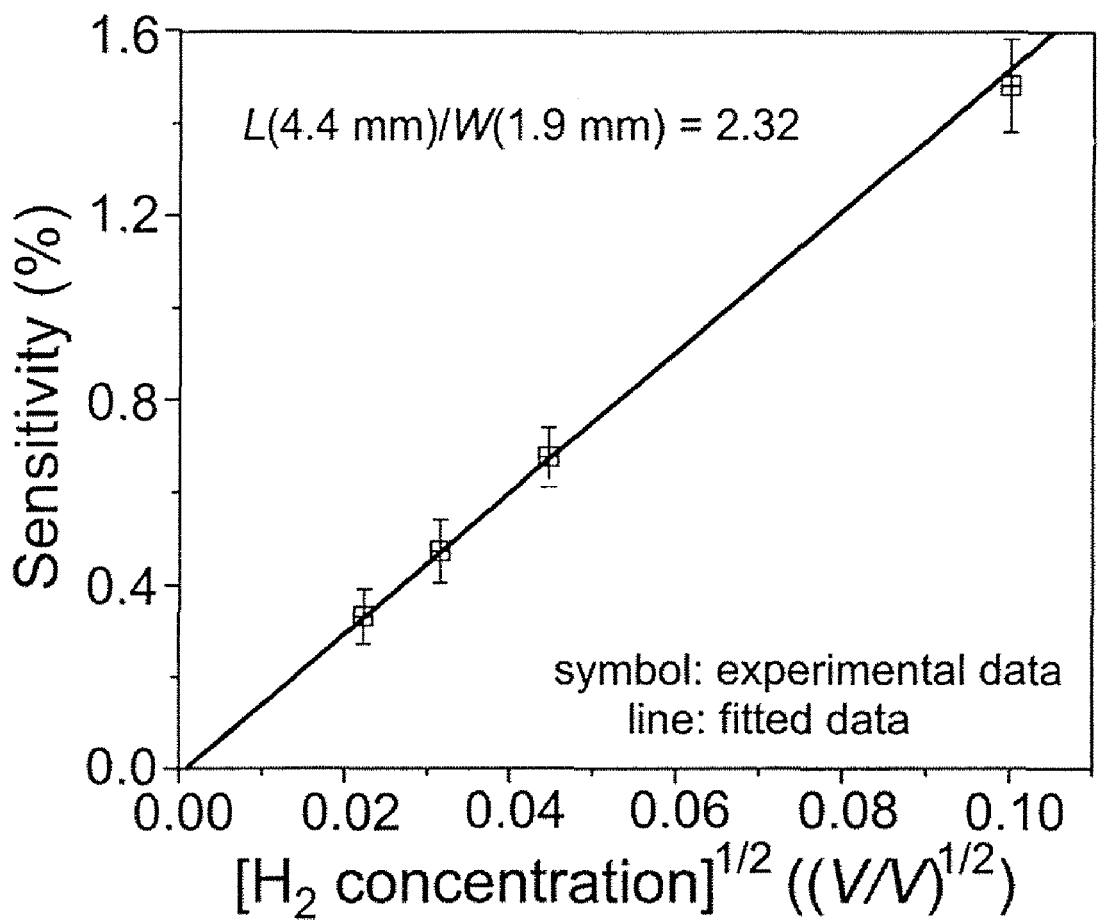
FIG. 9 is chart of sensitivities of hydrogen sensors comprising metallic pathways to the hydrogen concentration.

SWNTs grown through chemical vapor deposition (CVD) approaches are always a mixture of metallic and semiconducting ones. As a result, a network of SWNTs can exhibit either metallic or semiconducting charge transport behavior by controlling the ratio between the amount of semiconducting tubes and metallic tubes and/or the density of SWNTs. The SWNT networks used in the sensors (FIG. 7) with high sensitivities are mainly dominated by p-type semiconducting pathways for charge transport. This argument has been confirmed by the characteristic results of the thin-film transistors fabricated with the same SWNTs. In comparison, metallic SWNTs with much higher densities, which are dominated with metallic transport pathways (and have low resistance), are also used to fabricate devices through the same fabrication process. As shown in FIG. 9, the resulting hydrogen sensors (devices) exhibit much lower (by ~3 orders in magnitude) sensitivities toward hydrogen molecules compared with the sensors made of semiconducting SWNTs. The results imply that the charge transport behavior in semiconducting SWNTs is significantly modulated when the SWNTs/Pd composites are exposed to hydrogen. Therefore, SWNT networks dominated by semiconducting transport pathways are preferable for high-performance hydrogen sensors.

Figure 6:
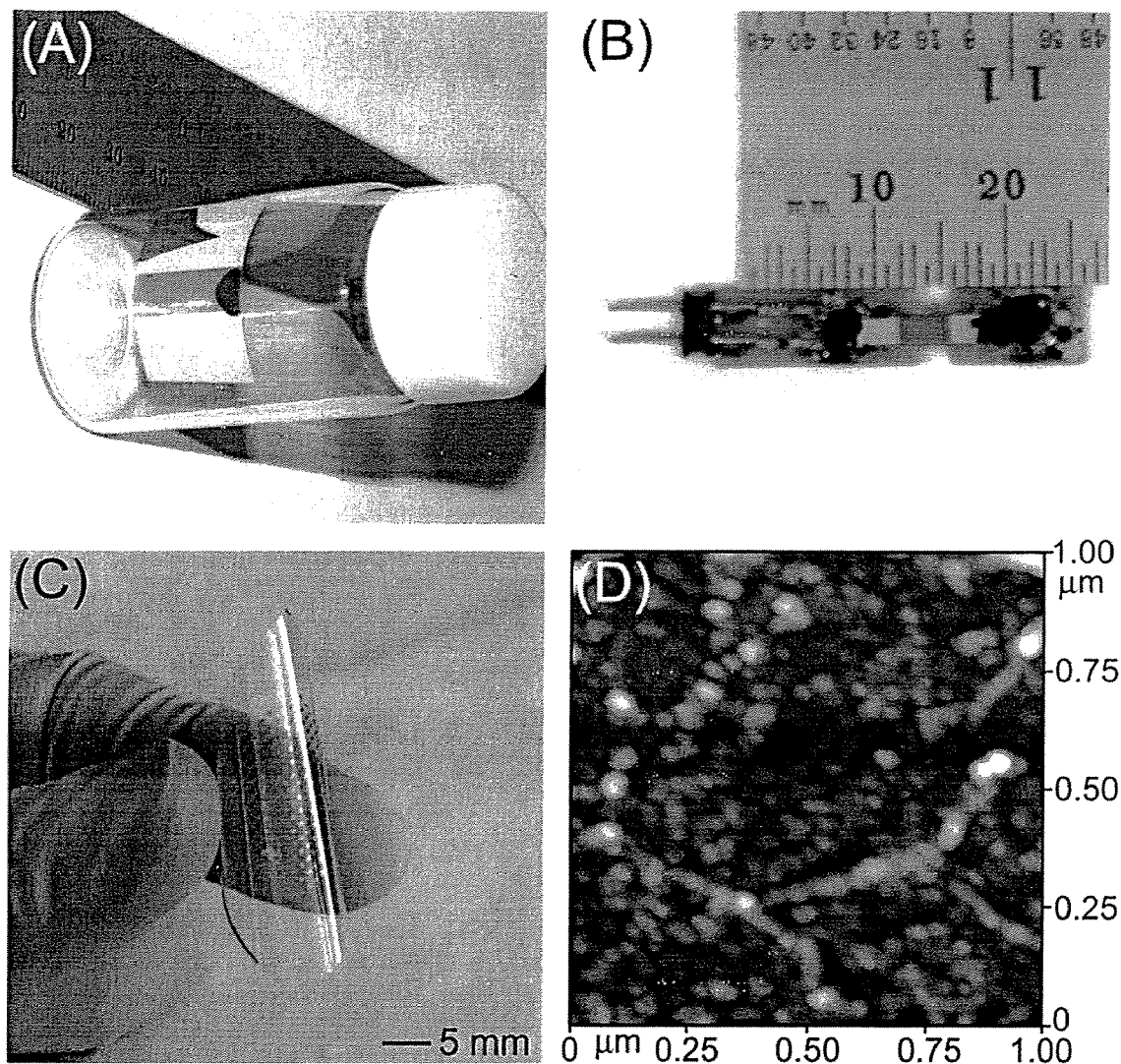
FIG. 6A illustrates a high-performance hydrogen sensor comformally laminated on a wall of a vial to illustrate its mechanical flexibility.
FIG. 6B illustrates the high-performance sensor mounted to a probe holder.
FIG. 6C shows a bent PET sheet with an array of hydrogen sensors.
FIG. 6D illustrates a typical AFM image of the channel region of a hydrogen sensor.
Figure 7:
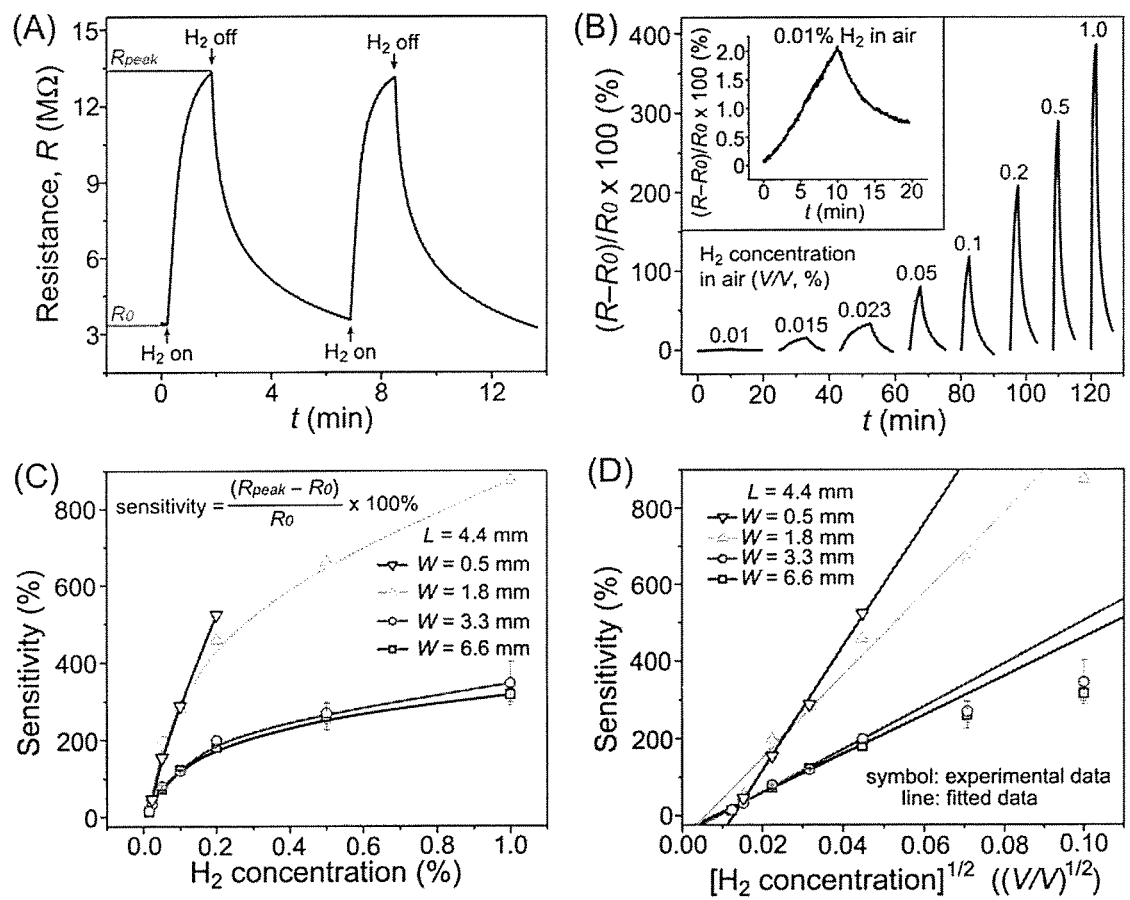
FIG. 7A is a chart showing the variation of resistance of a hydrogen sensor with channel length of 4.4 mm and channel width of 6.6 mm when the hydrogen with concentration of 5000 ppm is turned on and off for two cycles.
FIGS. 7B, 7C and 7D are charts that plot the response curves of the hydrogen sensors in hydrogen of different concentrations.

The SWNT networks used for the sensors shown in FIG. 6 can include both semiconducting (with high density) and metallic (with low density) pathways when their channels are wide. The ratio of the semiconducting to metallic pathways is important in determining the sensitivity of an as fabricated sensor because the metallic nanotubes decorated with Pd nanoparticles exhibit negligible response to hydrogen molecules (FIG. 9). Furthermore, too many metallic pathways can short the devices, leading to failure in sensing. Decreasing the aspect ratio of stripes of SWNT films can effectively eliminate the pure metallic pathways, thereby increasing the ratio of the semiconducting to the metallic pathways. The effect of aspect ratios (L/W) of the channels on the performance of the as-fabricated sensors are systematically evaluated.

The charts of FIGS. 7C and 7D compare the sensitivities of hydrogen sensors with same channel length (i.e., L=4.4 mm) and different channel widths. The results show that the hydrogen sensors with narrower channels have higher sensitivities, i.e., the sensors with higher aspect ratios exhibit higher sensitivities. Regardless of the aspect ratio, the sensitivities of a hydrogen sensor fit well a linear relationship against the square root of hydrogen concentration. A series of sensors with shorter channel length (i.e., L=1.0 mm) and different channel widths are also evaluated. The results (FIG. 10A) further confirm that the sensors with narrower channels have higher sensitivities.

Figure 8:
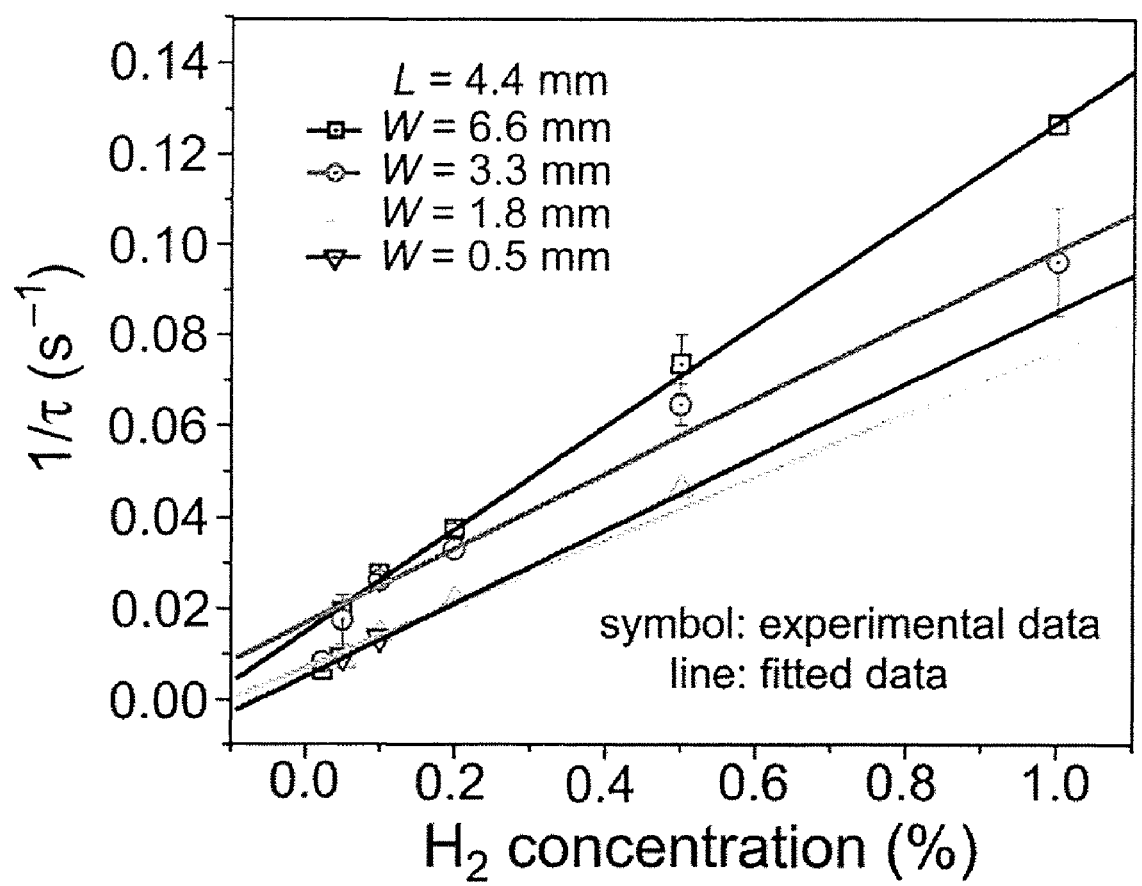
FIG. 8 is a chart of the reciprocal of the response time ($1/\tau$) to the hydrogen concentration.
Figure 10:
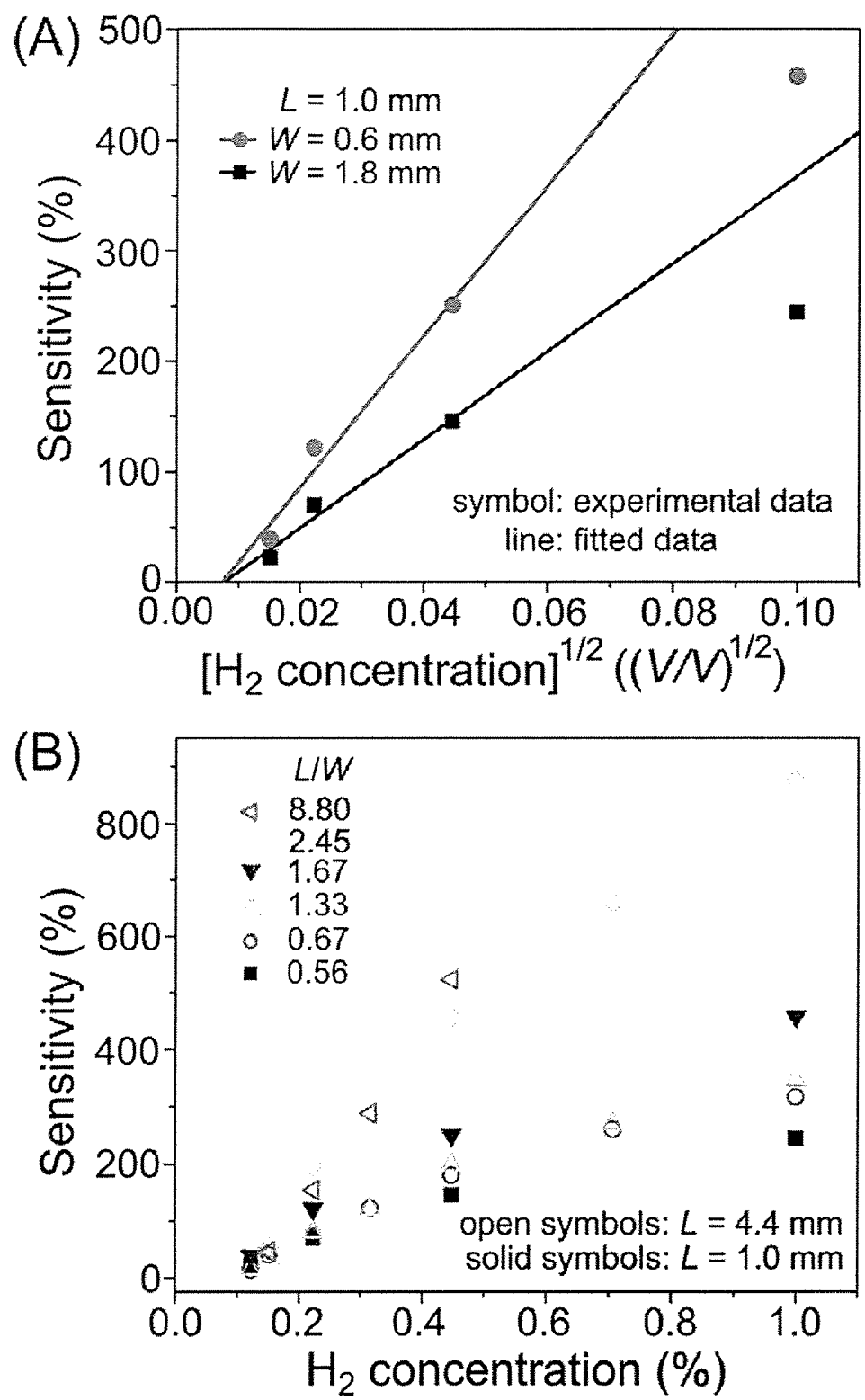
FIG. 10 are charts of sensitivity of hydrogen sensors comprising semiconducting pathways to the hydrogen concentration.

The sensitivities of the evaluated hydrogen sensors at different concentrations of hydrogen are plotted in FIG. 10B, clearly showing that the flexible hydrogen sensors become more sensitive with increase in aspect ratios of their channels. Different from the strong dependence of sensitivities on the aspect ratio of device channels, the response times of the high-performance flexible hydrogen sensors do not show significant variation for the sensors with different aspect ratios (FIG. 8). The results imply that the kinetics involved in the sensing process is approximately independent of the dimensions of the sensors and mainly determined by the reaction between hydrogen molecules and the Pd nanoparticles on the SWNTs.

The Pd nanoparticles on the surfaces of semiconducting SWNTs play an important role in probing hydrogen molecules because the SWNTs have weak interactions with hydrogen. This is confirmed because similar hydrogen sensors (devices) fabricated with pure SWNTs (without Pd nanoparticles) exhibit essentially no response upon exposure to hydrogen (FIG. 11B). As a result, the density and size of Pd nanoparticles, which are determined by the thickness of a Pd film deposited via electron-beam evaporation, influence significantly the performance of the sensors.

Figure 11:
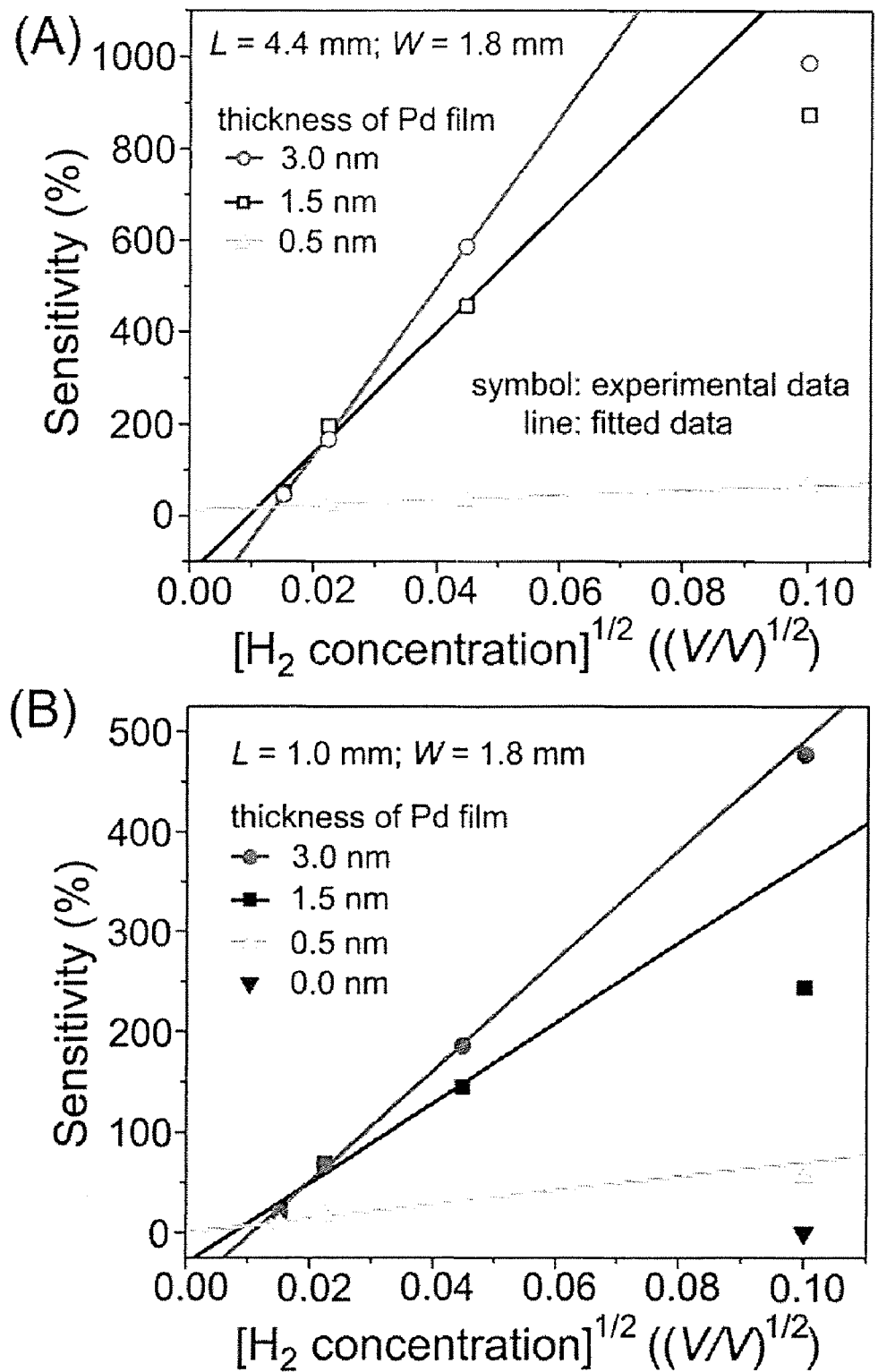
FIG. 11 are charts of the sensitivity of hydrogen sensors with different thicknesses of Pd films to the hydrogen concentration.

The charts of FIG. 11 compares the sensitivities of the hydrogen sensors made of SWNT networks decorated with Pd films that have different thicknesses. Both hydrogen sensors with different channel lengths display the same dependence on the thickness of modification Pd film, i.e., their sensitivities increase with the thickness of Pd film. The sensitivity increases by ~14 times (i.e., from 33% to 460%) for the sensor with L=4.4 mm and W=1.8 mm measured at hydrogen concentration of 0.2% when the thickness of the modification Pd film increases from 0.5 nm to 1.5 nm. However, the sensitivity of the hydrogen sensor with 3.0-nm Pd film is only 1.28 times of that of the sensor with 1.5-nm Pd film. The thick Pd film (with thickness of 3.0 nm) nucleates and grows into Pd nanoparticles with relatively large sizes and high densities compared with the thin Pd films. The high coverage of large Pd nanoparticles can contribute to the conductance of the sensors upon exposure to hydrogen molecules because the individual Pd nanoparticles can form continuous conduction pathways when they react with hydrogen and swell in their sizes. Different from the increase in resistance of the SWNT networks when the Pd nanoparticles react with hydrogen, the formation of new charge transport pathways in swollen Pd nanoparticles tends to decrease the resistance of the device, resulting in an adverse effect on sensing sensitivity. The synergistic effects account for the small increase in sensitivities of the sensors when the thickness of the Pd films is increased from 1.5 nm to 3.0 nm. Also, the formation of transport pathways in Pd nanoparticles is not suitable for bending operations because the gaps between Pd nanoparticles are changed (thus the resistance is changed) under bending status. Further increasing the thickness of Pd films generates continuous Pd wires, which exhibit sensitivities much lower than the SWNTs decorated with individual Pd nanoparticles. As a result, choosing appropriate thickness (for example, 1.5 nm is around the best value for the sensors shown in FIG. 11) of the films for modifying the SWNTs is important to achieve high sensitivities.

Figure 12:
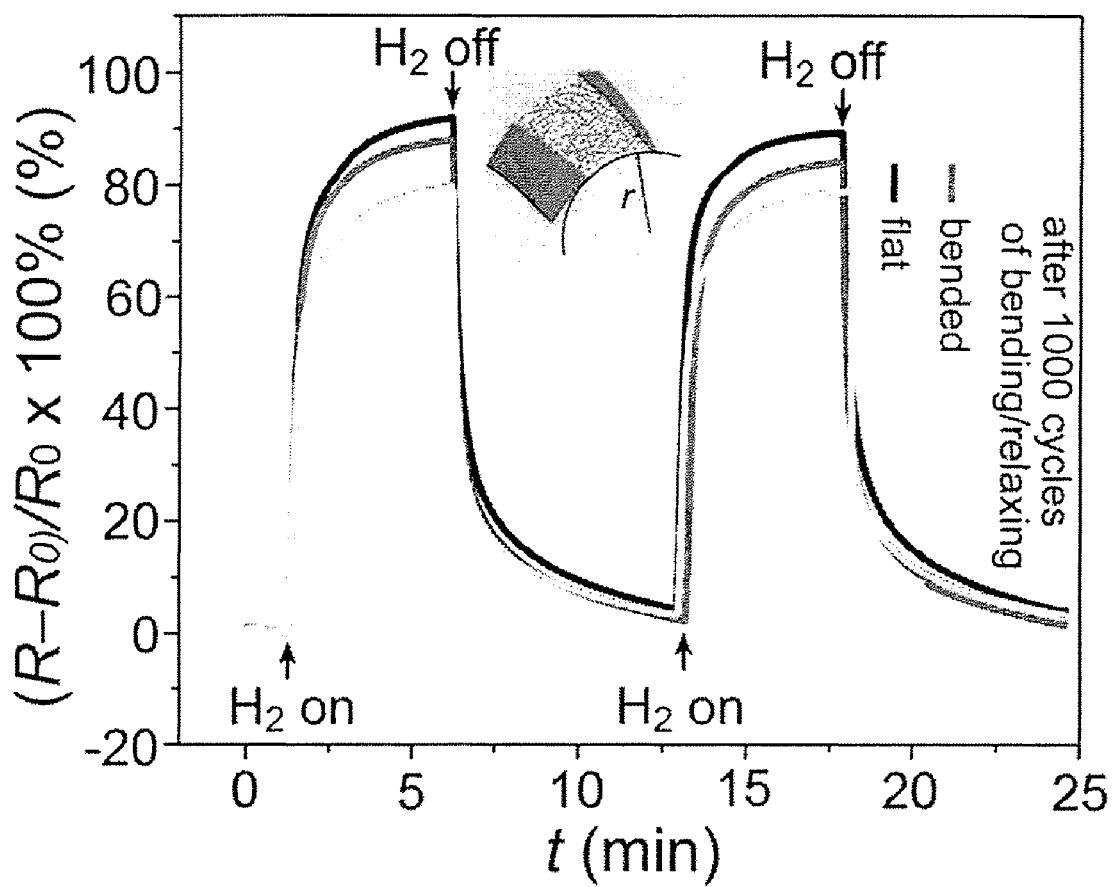
FIG. 12 compares the responses of a hydrogen sensor to 0.1% hydrogen in air when the sensor is flat and bended with a radium of ~2 mm.

Mechanical flexibility of the as-fabricated sensors represents an important parameter for practical applications in the envisioned areas where traditional sensors on rigid substrates are not suitable. The bending experiments can be carried out by laminating the hydrogen sensors on cylindrical surfaces of rods with various diameters. Flexibility of a sensor is evaluated by the bending radius (r) (inset of FIG. 12). The hydrogen sensors which can work at small bending radius exhibit high flexibility. The chart of FIG. 12 compares the responses of a hydrogen sensor to 0.1% hydrogen (in air) when it is flat (black curve) and bended with radius of ~2 mm. The hydrogen sensor of FIG. 12 is similar to that shown in FIG. 6B except that the probing electrodes comprise Ti (2 nm)/Pd (50 nm) bilayers. The curves of the chart of FIG. 12 show that bending the sensor does not affect its sensing performance significantly, i.e., no change in response time and a slight decrease (by 4.7%) in sensitivity. A fatigue test over this hydrogen sensor (device) indicates that its sensitivity decreases by only 13% even after it is compressed to a curved surface (with bending radius of ~2 mm) followed by relaxing to flat geometry for 1000 cycles. These results indicate that the sensors on PET substrates exhibit excellent mechanically bendability and durability. Furthermore, the sensing capability of the flexible hydrogen sensors does not degrade after they are stored in ambient environment at room temperature for ~6 months.

Figure 13:
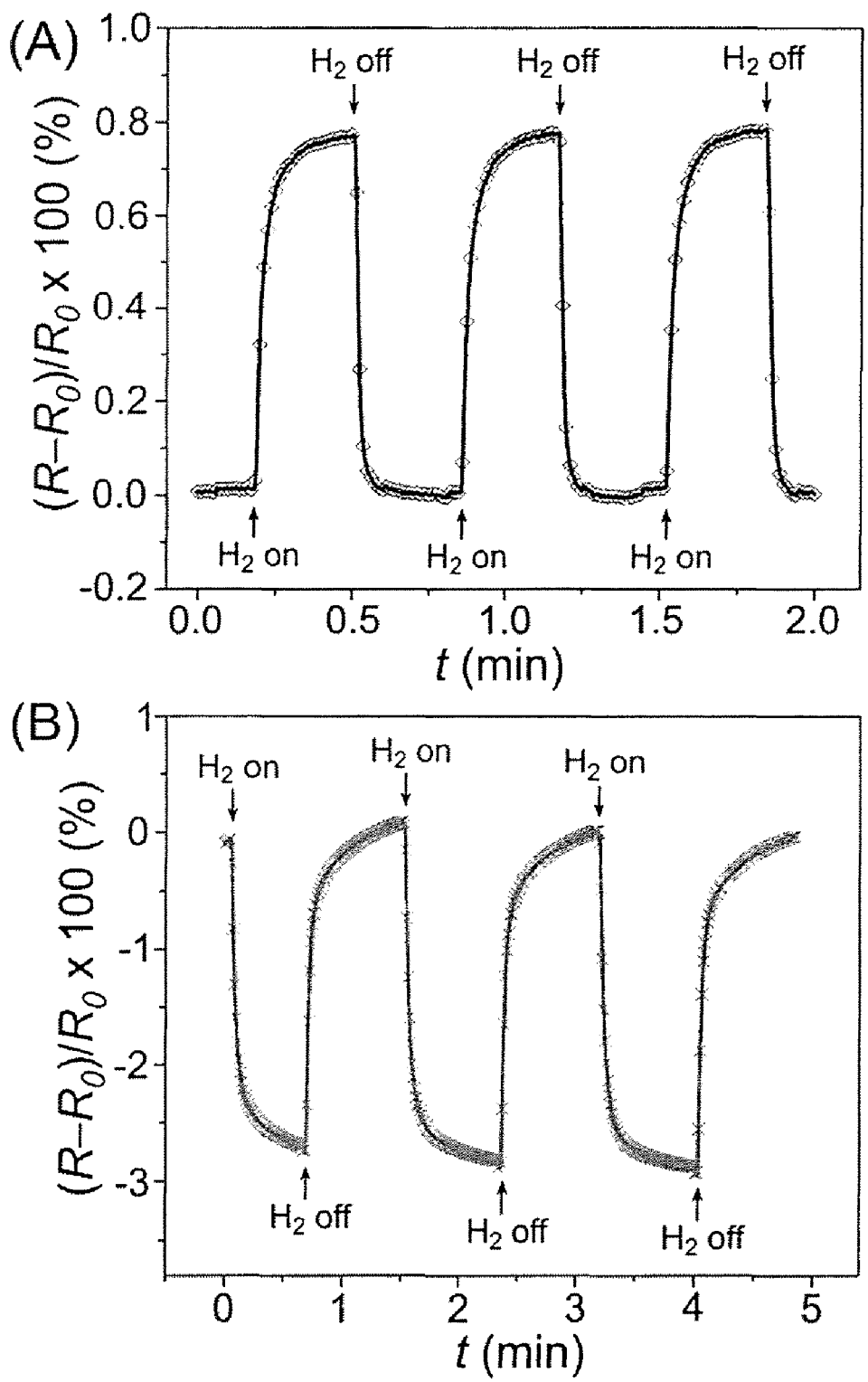
FIG. 13 are charts that illustrate the response curves of a hydrogen sensor made of pure Pd film with a thickness of 21 nm when it is measured on a flat surface.

The flexible hydrogen sensors fabricated with thin films of pure Pd on PET sheets are were evaluated before and after they were bent. The chart of FIG. 13A presents the response curve of a device made of pure Pd film with thickness of 21 nm when it is measured on a flat surface. The resistance increased by ~0.8% (much smaller than the sensors made of semiconducting SWNT/Pd composites) when the hydrogen sensor is exposed to hydrogen with concentration of 0.5% due to the conversion of pure Pd to palladium hydride (PdHx). However, the resistance of the sensor decreases by ~2.7% when it is bended at bending radius of 5 mm and exposed to 0.5% hydrogen (FIG. 13B). The latter response is consistent with hydrogen sensors made of discontinuous Pd beads or wires. This significant change in sensing behavior caused by bending might be ascribed to that a lot of cracks are generated in the Pd films when the sensor is bended. The comparison between results shown in FIG. 12 and FIG. 13 indicates that the SWNTs decorated with discrete Pd nanoparticles represent a class of promising building blocks for flexible hydrogen sensors with high performance.

Figure 14:
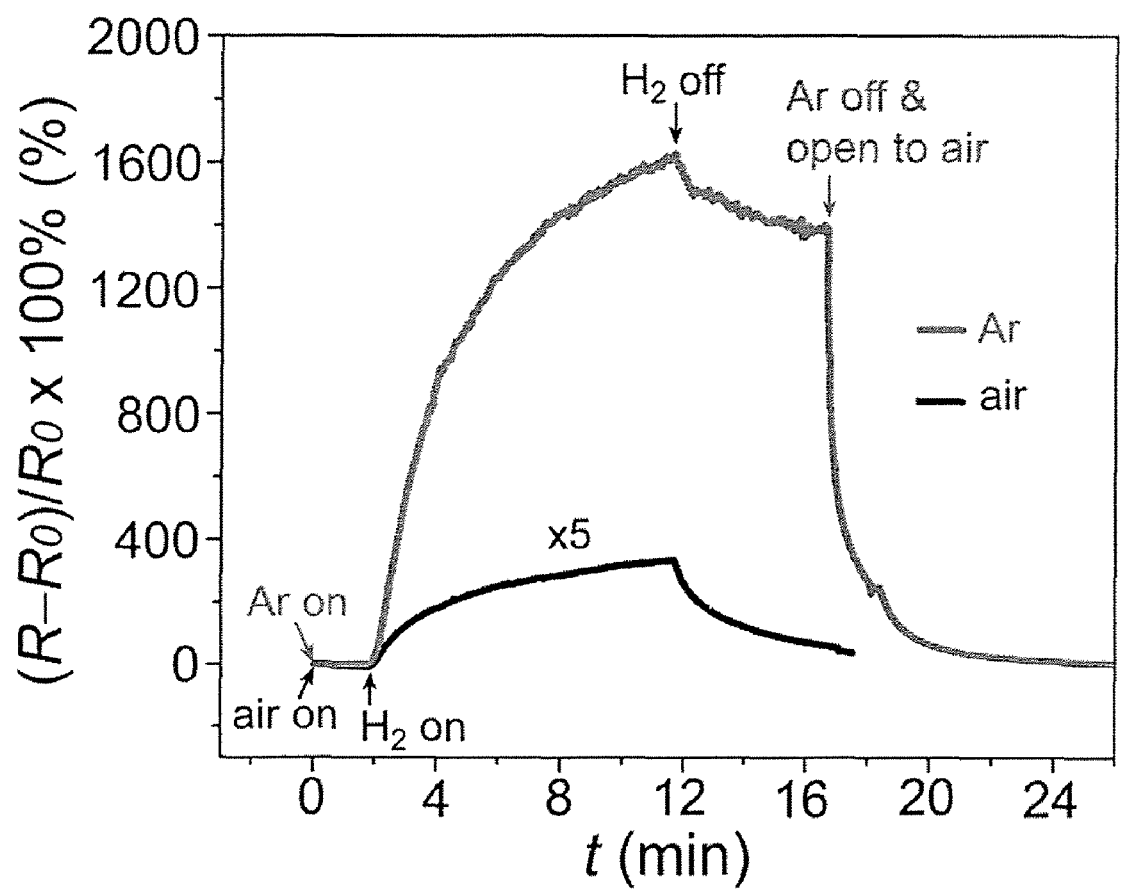
FIG. 14 is a chart that shows a hydrogen sensor in argon and in air.

In addition to hydrogen, oxygen molecules, which are one of the major components of air, actively react with Pd nanoparticles to form palladium oxide. In order to study the effect of oxygen molecules on the reaction between hydrogen molecules and Pd nanoparticles, the response curves of a hydrogen sensor upon exposure to hydrogen with fixed concentration (i.e., 0.05% in this case) in pure dry argon and dry air are compared in FIG. 14. The resistance of the sensor increases when hydrogen is introduced to both argon and air. Its resistance increases by 1620% of its original value after the sensor is exposed to hydrogen in argon for 10 min, while the resistance increases only by 67.2% of its original value after it is exposed to hydrogen in air. This large difference in resistance change implies that the oxygen molecules in air react with Pd nanoparticles to reduce the effective active Pd sites which can react with hydrogen molecules. The resistance of the sensor decreases quickly to its original value in air. However, the recovery process can be very slow in argon. Introducing air to the testing chamber accelerates the recovery process as shown in FIG. 14. The results indicate that the oxygen molecules in air reduce the sensitivity, but are beneficial to the quick removal of hydrogen in PdHx formed during sensing process.

SWNT networks dominated by semiconducting transport pathways are preferable for high-performance hydrogen sensors.

The inventive high-performance flexible hydrogen sensors produced unexpected surprisingly good results. High-quality semiconducting SWNTs grown by chemical vapor deposition (CVD) and printed onto plastic substrates by a dry transfer printing technique can provide building blocks for high-performance flexible hydrogen sensors. The separation of high-temperature growth and low-temperature printing/deposition helps enable the fabrication of the flexible hydrogen sensors with SWNTs on plastics. SWNTs decorated with discrete Pd nanoparticles on PET sheets provide useful building blocks for producing high-performance flexible hydrogen sensors based on the change of resistance in the SWNTs. The as-fabricated flexible hydrogen sensors exhibit high sensitivities, which are comparable to or even higher than traditional sensors fabricated on rigid substrates. The high-performance flexible hydrogen sensors exhibited a fast response and recovery behaviors when operated in air at room temperature.

Systematic evaluations reveal that increasing the aspect ratio (L/W) between the channel lengths and channel widths of the as-fabricated hydrogen sensors leads to enhanced sensitivity. Advantageously, the material cost for the use of SWNTs/Pd composites for high-performance flexible hydrogen sensors is much lower than those made of pure palladium (Pd) films or Pd nanotubes/nanowires. Replacing electron-beam evaporation (EBE) with electrochemical deposition can selectively deposit Pd nanoparticles only on the surfaces of the SWNTs, rather than the whole surface of the sensors, thereby decreasing the usage of expensive Pd. Desirably, operating the high-performance flexible hydrogen sensors at bending radius of several millimeters and for thousands of bending/relaxing cycles do not result in significant degradation in sensing performance. These results indicate that the as-fabricated hydrogen sensors provide superior sensing performance and excellent mechanical flexibility and can be useful for applications requiring light weight, conformal wrapping on curvilinear surfaces, and mechanical shock resistance.

As discussed previously, flexible hydrogen sensors can be fabricated by growing networks of single walled carbon nanotubes (SWNTs) using chemical vapor deposition (CVD), decorating the SWNTs with palladium (Pd) nanoparticles using electron beam deposition or electrochemical deposition, and printing the Pd decorated SWNT networks on plastic substrates using a low-temperature process. By taking advantage of the low temperature, dry transfer printing technique and combining it with the high temperature preparation of the high-quality SWNT networks, flexible hydrogen sensors can be manufactured with performance superior to traditional sensors fabricated of pure palladium materials.

The performance of the flexible hydrogen sensors meets the U.S. Department of Energy (DOE) 2015 energy goals for sensors. The resistivity change of the high-performance flexible hydrogen sensors can be almost 100% for 0.1% (volume/volume) hydrogen in air at room temperature. Response times for the high-performance flexible hydrogen sensors can be about 1.5 seconds for 1% hydrogen and the high-performance flexible hydrogen sensors can be completely recovered within one (1) minute. The high-performance flexible hydrogen sensors have been shown to detect hydrogen in concentrations as low as 30 ppm. The high-performance flexible hydrogen sensors can continue to operate effectively even when in a bent or curved configuration. Fatigue tests where the sensors were bent and relaxed 2000 times have shown that the high-performance flexible hydrogen sensors are durable and maintain their performance despite mechanical stress.

High-performance flexible hydrogen sensors have excellent sensing properties. For example, a resistance change of 75% can be produced when the high-performance flexible hydrogen sensors are exposed to small amounts of hydrogen, such as 0.05% hydrogen in air. The high-performance flexible hydrogen sensors also have a fast response time, such as at 1.5 seconds and a quick recovery time, such as at one (1) minute for 1% hydrogen. The use of SWNTs and palladium (Pd) particles significantly lowers the fabrication costs of the inventive sensors compared to conventional sensors made with expensive films of pure Pd. Using plastic sheets as the substrates on which the sensors are built can also reduces the overall weight of the high-performance flexible hydrogen sensors, as well as helps increase their mechanical strength and shock resistance. Desirably, the high-performance hydrogen sensors are flexible and capable of being bent into curved shapes.

The high-performance flexible hydrogen sensors can be useful for hydrogen-fueled space shuttles. In particular, the hydrogen-fueled space shuttles can be covered with large-area flexible hydrogen sensor arrays on plastic sheets to reduce the overall weight and to detect any leakage of hydrogen.

Among the many advantages of the high-performance flexible hydrogen sensors are:
1. Superior sensing of hydrogen at ambient temperature
2. Superb capabilities for moderate temperature operations.
3. Enhanced response and recovery time.
4. Excellent flexibility and bending.
5. Greater versatility.
6. Outstanding performance.
7. Reliable.
8. Readily transportable.
9. Light weight.
10. Portable.
11. User friendly.
12. Easy to fabricate.
13. Durable
14. Economical.
15. Attractive.
16. Efficient.
17. Effective.
18. Low cost.
19. High sensitivity.
20. Wide sensing range.
21. Be able to form large area arrays
22. Transparency of the sensing regions Although embodiments and examples of the invention have been shown and described, it is to be understood that various modifications, substitutions, and rearrangements of parts, components, and/or process (method) steps, as well as other uses of high-performance flexible sensors and process, can be made by those skilled in the art without departing from the novel spirit and scope of this invention.

What is claimed is:

1. Flexible hydrogen sensors, comprising:
high temperature chemical vapor deposition (CVD) single-walled carbon nanotubes (SWNTs) with clean surfaces;
flexible plastic substrates for supporting said SWNTs;
palladium (Pd) nanoparticles on said SWNTs, said Pd nanoparticles being spaced from each other to form individual discontinuous Pd nanoparticles rather a continuous Pd film;
two metal electrodes of gold, said gold electrodes being positioned on SWNTs and said gold electrodes being spaced and separated from each other;
said gold electrodes arc covered and coated with insulating silicon dioxide $SIO_2$ film;
no Pd nanoparticles are deposited on said gold electrodes because said gold electrodes are covered with said $SiO_2$ film:
said SWNTs and said Pd nanoparticles having variable resistance for conversion and amplification into electrical signals;
said SWNTs and Pd nanoparticles cooperating with each other to provide high-performance flexible hydrogen sensors for sensing hydrogen; and
said high-performance flexible hydrogen sensors being bendable for conforming and complementing contours of other structures while substantially maintaining performance.

2. Flexible hydrogen sensors in accordance with claim 1 fabricated by high-vacuum evaporation comprising electron beam evaporation (EBE) and/or thermal evaporation; said Pd nanoparticles are first deposited on said SWNTs and said gold electrodes are sequentially deposited on said flexible plastic substrates.

3. Flexible hydrogen sensors, comprising:
high temperature chemical vapor deposition (CVD) single-walled carbon nanotubes (SWNTs) with clean surfaces;
flexible plastic substrates for supporting said SWNTs;
palladium (Pd) nanoparticles on said SWNTs, said Pd nanoparticles being spaced from each other to form individual discontinuous Pd nanoparticles rather a continuous Pd film;
two metal electrodes of gold, said gold electrodes being positioned on SWNTs and said gold electrodes being spaced and separated from each other;
said SWNTs and said Pd nanoparticles having variable resistance for conversion and amplification into electrical signals;
said SWNTs and Pd nanoparticles cooperating with each other to provide high-performance flexible hydrogen sensors for sensing hydrogen;
said high-performance flexible hydrogen sensors being bendable for conforming and complementing contours of other structures while substantially maintaining performance;
said flexible hydrogen sensors are fabricated by electrochemical deposition comprising electrochemical reactions on the surfaces of said SWNTs;
said Pd nanoparticles are selectively deposited on the surfaces of said SWNTs exposed to electrolyte solution;
said gold electrodes are covered and coated with insulating silicon dioxide ($SiO_2$) film; and
no Pd nanoparticles are deposited on said gold electrodes because said gold electrodes are covered with said $SiO_2$ film.

4. Flexible hydrogen sensors in accordance with claim 3 comprising smaller flexible hydrogen sensors which are post-cut after fabrication from larger flexible hydrogen sensors.

5. Flexible hydrogen sensors in accordance with claim 3 wherein said flexible hydrogen sensors are post-cut and sliced into narrower flexible hydrogen sensors.

6. Flexible hydrogen sensors in accordance with claim 3 wherein said SWNTs have a controllable resistance which is tuned by CVD and by coating and contacting the SWNTs with said Pd nanoparticles.

7. Flexible hydrogen sensors in accordance with claim 3 having a sensitivity with detection limits as low as 500 ppm hydrogen and a response time as low as about 3 seconds.

8. Flexible hydrogen sensors in accordance with claim 3 comprising high-performance flexible hydrogen sensors which maintain their performance after storage in an ambient environment for six (6) months.

9. Flexible hydrogen sensors in accordance with claim 3 comprising:
- high-performance flexible hydrogen sensors having a bending; and
- said flexible hydrogen sensors maintain their bending radius and performance during 2000 bending and relaxing cycles.

* * * * *